(12) United States Patent
Suzuki et al.

(10) Patent No.: US 7,421,059 B2
(45) Date of Patent: Sep. 2, 2008

(54) X-RAY COMPUTER TOMOGRAPHY APPARATUS

(75) Inventors: Masakazu Suzuki, Kyoto (JP);
Takahiro Yoshimura, Kyoto (JP);
Masanobu Yoshida, Kyoto (JP);
Masanori Otsuka, Kyoto (JP); Hideki Yoshikawa, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 121 days.

(21) Appl. No.: 10/510,887

(22) PCT Filed: Apr. 10, 2003

(86) PCT No.: PCT/JP03/04593

§ 371 (c)(1),
(2), (4) Date: Feb. 9, 2005

(87) PCT Pub. No.: WO03/084407

PCT Pub. Date: Oct. 16, 2003

(65) Prior Publication Data

US 2005/0117696 A1 Jun. 2, 2005

(30) Foreign Application Priority Data

Apr. 11, 2002 (JP) .............................. 2002-109645

(51) Int. Cl.
*A61B 6/14* (2006.01)
(52) U.S. Cl. ............................. 378/39; 378/38; 378/40
(58) Field of Classification Search .................. 378/38, 378/39, 40
See application file for complete search history.

(56) References Cited

U.S. PATENT DOCUMENTS

| 5,386,446 | A | * | 1/1995 | Fujimoto et al. | 378/20 |
| 6,118,842 | A | * | 9/2000 | Arai et al. | 378/39 |
| 6,493,415 | B1 | * | 12/2002 | Arai et al. | 378/39 |
| 2001/0021244 | A1 | * | 9/2001 | Suzuki et al. | 378/196 |

FOREIGN PATENT DOCUMENTS

| JP | 10-225455 | 8/1988 |
| JP | 7-136158 | 5/1995 |
| JP | 8-215182 | 8/1996 |
| JP | 2000-139902 | 5/2000 |
| JP | 2002-85400 | 3/2002 |
| WO | WO 200057789 A1 * | 10/2000 |

* cited by examiner

*Primary Examiner*—Chih-Cheng G Kao
(74) *Attorney, Agent, or Firm*—William L. Androlia; H. Henry Koda

(57) ABSTRACT

An X-ray CT apparatus which executes a first X-ray tomography on a sectional plane having a desirable thickness in an object to be examined (0) with the object interposed between an X-ray generator (1) and a two-dimensional X-ray image sensor (2) provided so as to hold their mutual facing positional relation, and also executes a second X-ray tomography for obtaining a CT image of the interested area of the object (0). The first X-ray tomography is executed on the object (0) while the object (0) is held and fixed by an object holder (4) with the center of the orbit of the X-ray circulating radiation fixed, and while the object holder (4) is moved by an object mover (5) along the X-ray sectional image forming path according to the rotary angle of the X-ray circulating radiation.

21 Claims, 25 Drawing Sheets

X-RAY COMPUTER TOMOGRAPHY APPARATUS

TECHNICAL FIELD

The present invention relates to an X-ray CT apparatus in which the center of the orbit of X-ray circulating radiation is fixed on an imaging interested area in an object, X-ray is radiated in a circulating manner only on the imaging interested area, and the second X-ray sectional image which is an X-ray image obtained by reconstructing an X-ray absorption coefficient of the imaging interested area, and further, the first X-ray sectional image such as a curved plane X-ray sectional image and a flat plane X-ray sectional image can be produced.

BACKGROUND ART

In the field of dental treatment such that a local area to obtain CT image, namely an imaging interested area, is only a part of a relatively small area like a human head, for example one or two teeth, an X-ray CT apparatus in which an X-ray rotary center is fixed on the imaging interested area, X-ray is radiated in a circulating manner only on the imaging interested area and the image of the X-ray absorption coefficient of the imaging interested area has been heavily used recently because its X-ray dosing amount on a patient is remarkably reduced comparing to a prior art and the apparatus is small sized because of vertical rotary center.

In this filed, there has been a large demand of a curved plane sectional image which is a transmitted X-ray image of a curved sectional area of an entire dental arch and an X-ray CT apparatus capable of obtaining a curved plane X-ray sectional image has been provided. The curved plane X-ray sectional image of the curved sectional area of an entire dental arch is called as a dental X-ray panoramic image.

For example, in the X-ray CT apparatus disclosed in JP-A-10-225455 by the present applicant, a curved plane X-ray tomography is executed by moving an X-ray rotary center during X-ray radiation and an X-ray CT is executed when the X-ray rotary center is fixed on the area of an object to obtain a CT image, namely an imaging interested area. However, the X-ray rotary center is designed to be movable for the curved plane X-ray tomography, so that mechanical accuracy required for fixing the rotary center during X-ray CT is not strictly held because of backlash of a gear. Therefore, the adverse effect on the accuracy of CT image caused by deflection of the X-ray rotary center has not been ignored, thereby causing the affect on X-ray CT by using both as the curved plane X-ray tomography apparatus and as the X-ray CT apparatus.

The X-ray CT apparatus disclosed in JP-A-2000-139902 is proposed by the applicant of the present invention, in case of curved plane X-ray tomography, the X-ray rotary center is fixed on the center of a virtual local region which includes all the orbit of X-ray required for obtaining prior curved plane X-ray sectional image, conical X-ray beam is radiated on the virtual local region, and thus obtained X-ray transmitted images are patched together to obtain the curved plane X-ray sectional image similar to the prior art.

However, in this apparatus, slit control for radiating X-ray conical beam is complicated and the distance between the X-ray rotary center and the tooth is different depending on the position in the dental arch, thereby requiring to arrange the pace of expansion to obtain the same size images as a whole.

Further in this apparatus, when an X-ray transmitted image is backprojected, a three-dimensional X-ray absorption coefficient of the dental arch is calculated and the curved plane X-ray sectional image can be obtained by reconstructing the coefficient, however, the length of process time has been problem.

Therefore, the X-ray CT is a main object of the invention, thereby causing adverse effect to the curved plane X-ray tomography.

Any one of the above-mentioned X-ray CT apparatus is capable of curved plane X-ray tomography in addition to X-ray CT, however, it cannot execute both a curved plane X-ray tomography and an X-ray CT as well as an exclusive apparatus for curved plane X-ray tomography or X-ray CT, or more preferable than it. Further, the apparatus cannot achieve smooth link of both tomography such that a local X-ray CT is executed utilizing the result of curved plane X-ray tomography while an object is fixed to the apparatus.

In JP-B-2-29329 proposed by the applicant of the present invention, an X-ray imaging apparatus has been disclosed such that a panoramic X-ray imaging for a dental arch is executed with an X-ray image sensor comprised of an X-ray multiplier. In this apparatus, a panoramic radiography on the curved plane along the dental arch has been possible, however, X-ray CT has not been possible.

DISCLOSURE OF THE INVENTION

The present invention has been proposed in order to solve the above-mentioned problems. The object of the present invention is to provide an X-ray CT apparatus achieving the integration of the first and the second tomography in which the apparatus is a complex type such that the first X-ray tomography like a curved plane X-ray tomography and a flat plane X-ray tomography and the second X-ray tomography such as X-ray CT are possible, on the other hand the first tomography and the second tomography are possible like a prior art, and a smooth link of these X-ray tomography is possible.

(1) The present invention proposes an X-ray CT apparatus having an X-ray radiation means comprising an X-ray generator and a two-dimensional X-ray image sensor. X-ray beam is radiated on an object to be examined, while the X-ray generator and the X-ray image sensor moves for X-ray circulating radiation relative to each other with an object to be examined interposed therebetween so as to hold their mutual facing positional relation. A first X-ray tomography is executed for obtaining a curved plane tomography image or a flat plane tomography image, whereas a second X-ray tomography is executed for obtaining a computed tomography image of an interested area of the object. The X-ray computer tomography apparatus is comprised of an object holding means and an object moving means. The first X-ray tomography is executed in a manner that the object holding means is moved by the object moving means depending on a rotary angle of X-ray circulating radiation while holding the object by the object holding means during the X-ray circulating radiation, with the center of the orbit of the X-ray circulating radiation fixed.

The first X-ray tomography refers to an imaging method for obtaining the transmitted X-ray image of a sectional plane which is supposed on in an object and has a desirable thickness of several millimeter and width included in the size of a tooth being an imaging object. The resulted image is called as the first X-ray sectional image. In the field of dentistry, the radiography in which the object is a dental arch and the imaging object is a curved sectional plane on the dental arch is specifically referred to a dental panoramic radiography and includes radiography for obtaining the curved plane sectional image of temporomandibular joint and a curved plane X-ray tomography of auditory ossicle in otolaryngology.

The first X-ray tomography includes a flat plane X-ray tomography such as a cross section radiography or a tangential radiography for obtaining the image of a flat sectional plane which is perpendicular to the dental arch or has a predetermined thickness along the tangential direction of the dental arch.

As a method of flat plane X-ray tomography, a wide-area two-dimensional X-ray image sensor like MOS sensor is used and a flat plane sectional image may be produced on the two-dimensional image sensor by TDI, described later, while the two-dimensional X-ray image sensor is fixed and only an X-ray generator is moved.

Thus, the first X-ray tomography executes imaging of the X-ray sectional plane having a thickness corresponding to the thickness of the imaging object like a tooth, a dental arch, a temporomandibular joint, an auditory ossicle and so on.

The second tomography refers to CT on the imaging interested area of the object.

The X-ray rotary center refers to the center of rotation when the X-ray generator and the two-dimensional X-ray image sensor facing each other are turned around the object to radiate X-ray on the object.

In this X-ray CT apparatus, the object holding means for fixing the object is moved by the object moving means along the orbit for producing the first X-ray sectional image corresponding to the rotary angle of the rotary arm while X-ray is radiated in a circulating manner for obtaining the first X-ray sectional image.

Therefore, because the center of the orbit of the X-ray circulating radiation is held and fixed in the first X-ray tomography with this apparatus, the rotary center does not cause deflection, so that the accuracy of the second X-ray tomography, namely X-ray CT, is not deteriorated because of the deflection. Further, because the object is moved along the orbit for obtaining the first X-ray sectional image, the X-ray transmitted image obtained by radiation is patched as it is without arranging the pace of expansion or without executing the time-consuming back projection, thereby obtaining the X-ray sectional image on a curved plane or a flat plane like an prior art in a short time.

(2) Further, the present invention proposes An X-ray computer tomography apparatus having an X-ray radiation means comprising, an X-ray generator, a two-dimensional X-ray image sensor and a circulating means for circulating the X-ray generator and the two-dimensional X-ray image sensor. A first X-ray tomography is executed for obtaining a curved plane tomography image or a flat plane tomography image in a manner that the X-ray generator and the two-dimensional X-ray image sensor are moved relative to each other with an object to be examined interposed therebetween so as to hold their mutual facing positional relation, whereas a second X-ray tomography is executed for obtaining a computed tomography image of an interested area of the object. The X-ray computer tomography apparatus is comprised of an object holding means for holding the object; and an object moving means for moving the object holding means fixed depending on the rotary angle of the X-ray circulating radiation during the X-ray circulating radiation, with the center of the orbit of the X-ray circulating radiation fixed, when executing the first X-ray tomography of the object.

In this X-ray CT apparatus, it is cleared that the circulating means is provided for the X-ray radiation means of (1) for rotating the X-ray generator and the two-dimensional image sensor.

The circulating means is designed to turn a rotary arm but may be provided with a gantry. In the gantry type, a patient is usually laid on a bed during imaging, so that the object holding means is a bed which is moved up and down or side by side in two-dimensionally or three-dimensionally. Or when a patient is laid, a rotary arm called C arm is turned on a perpendicular plane around the imaging target region of the patient.

Like the preferred embodiment of the present invention, a circulating means may be constructed such that a patient sits or stands up and the circulating means is turned on a horizontal plane around the imaging target region of the patient. Or it may be constructed such that a patient is laid and the circulating means is turned on a perpendicular plane around the imaging target region of the patient.

(3) Still further, the X-ray computer tomography apparatus mentioned in (1) and 2) is comprised of an image processing means for producing the X-ray sectional image by executing Time Delay Integration (TDI) process to the X-ray transmitted image detected by the two-dimensional X-ray image sensor in the first X-ray tomography, which is transmitted through the object by radiating X-ray from the X-ray generator; and an object moving means for moving the X-ray radiation means or the object holding means.

The X-ray tomography apparatus using the TDI method has been detailed in JP-A-8-215182 which has been filed by the applicant of the present invention and its principle is explained in JP-B-2-29329 which has been also filed by the applicant of the present invention. The technology disclosed in these publications can be used as a preferable embodiment of the present invention.

The X-ray CT apparatus is characterized in that Time Delay Integration is executed on the X-ray sectional image during X-ray tomography described in (1) and (2).

(4) According to the above-mentioned X-ray CT apparatus described in (1)-(3), the first X-ray tomography is executed for obtaining an X-ray sectional image including a blurred image of the regions other than the target sectional area thorough a curved plane tomography or a flat plane tomography in a manner that the X-ray generator and the two-dimensional X-ray image sensor are moved relative to each other with an object to be examined interposed therebetween so as to hold their mutual facing positional relation. The second X-ray tomography is executed for obtaining an X-ray sectional image excluded a blurred image through a computed tomography which computes and processes a three-dimensional X-ray absorption coefficient data.

In this X-ray CT apparatus, the X-ray absorption distribution information of the sectional plane is digitally obtained for the X-ray sectional image of the interested area in obtained by the second X-ray tomography and an X-ray sectional image without a blurred image can be obtained by the X-ray absorption distribution information. Therefore, in the tomography on the interested area which is usually required to obtain an accurate X-ray sectional image, the X-ray sectional image excluding the blurred image can be obtained to contribute an accurate diagnosis.

Any one of the methods disclosed in JP-A-10-225455, JP-A-2000-139902, JP-B-2-29329, which are mentioned above, JP-A-9-140701, JP-B-2824602, or JP-A-7-308314 may be used as a method for obtaining the first X-ray sectional image such as the curved plane X-ray sectional image and the flat plane X-ray sectional image including the blurred image. Any method applicable for the embodiment of the first X-ray sectional image of the present invention is used.

(5) According to the above-mentioned X-ray CT apparatus described in (2)-(4), relative movement between the X-ray generator and the two-dimensional X-ray image sensor is a rotary movement or a parallel movement.

As a mechanism for parallel movement, a mechanism for executing a flat plane X-ray tomography while the X-ray generator and the X-ray detector are moved in parallel may be added to the rotary arm applicable to a panoramic X-ray radiography or X-ray CT in which the X-ray generator and the X-ray detector are positioned so as to face each other.

JP-A-7-136158 filed by the applicant of the present invention discloses an apparatus applicable to both panoramic radiography and flat plane X-ray tomography in which a mechanism for executing a flat plane X-ray tomography while the X-ray generator and the X-ray detector are moved in parallel is added to the rotary arm for a panoramic X-ray radiography or X-ray CT in which the X-ray generator and the X-ray detector are provided so as to face each other. The disclosed mechanism can be applied to the preferable embodiment of the present invention.

(6) According to the above-mentioned X-ray CT apparatus described in (1)-(5), the second X-ray tomography is executed for obtaining an X-ray computed tomography image around a local region of the object in a manner that the interested area of the object conforms to the rotary center of X-ray circulating radiation by moving the object holding means or the X-ray radiation means after the first X-ray tomography is finished.

(7) According to the above-mentioned X-ray CT apparatus described in (1)-(6), the X-ray computed tomography apparatus is comprised of: a display means on which the first X-ray sectional image of the object taken by the first X-ray tomography is displayed and an interested area selection means for selecting the interested area to be taken by the second X-ray tomography on the first X-ray sectional image displayed on the display means, and a calculation means of rotary center position for calculating movement data for relatively moving the object holding means or the X-ray radiation means in a manner that the X-ray rotary center conforms to the interested area selected by the interested area selection means. The object holding means or the X-ray radiation means is moved depending on the movement data, and thereafter the X-ray radiation means is circulated with the center of the orbit of the X-ray circulating radiation fixedly conformed to the interested area during X-ray circulating radiation, thereby executing the second X-ray tomography.

This characteristic is applicable to the X-ray CT apparatus in which the X-ray generator and the two-dimensional image sensor are moved while fixing the object, the apparatus in which the object is moved while fixing the rotary center of the X-ray generator and the two dimensional image sensor, or the apparatus having both functions.

(8) According to the above-mentioned X-ray CT apparatus described in (1)-(7), the object holding means has a chair for holding a patient in sitting position and a head fixing means at the upper part of the chair, and the object holding means further has a pulse motor for moving the object in an axial direction of an X-ray rotary axis or in a vertical direction to the X-ray rotary axis.

Further, in this X-ray CT apparatus, the construction of the object holding means is specifically defined and the apparatus is preferably used when a patient sits on the chair with his head fixed and the head is an object to be imaged. Of course, other embodiment in which the object holding means is a bed type for holding a laid patient may not be excluded.

(9) According to the above-mentioned X-ray CT apparatus described in (8), the X-ray radiation means has a rotary arm rotatable around the rotary center, the rotary arm holds the X-ray generator and the two-dimensional X-ray imaging sensor so as to keep their mutual facing positional relation. The first X-ray tomography is executed for obtaining a curved plane sectional image in a manner that the rotary arm turns around the object with the center of the orbit of the X-ray circulating radiation fixed during its tomography, while the chair is moved along a predetermined imaging orbit in synchronism with the turning of the rotary arm.

(10) According to the above-mentioned X-ray CT apparatus described in (1)-(8), the first X-ray tomography is executed for obtaining a flat plane sectional image by mutually moving the X-ray generator and the two-dimensional X-ray image sensor held by a rotary arm in a direction opposite to each other, while turning the rotary arm around the object with the interested area interposed therebetween.

(11) According to the above-mentioned X-ray CT apparatus described in (1)-(9), the second X-ray tomography is executed for obtaining X-ray computer tomogprahy image of the local region of the object by radiating conical X-ray beam from the X-ray generator.

(12) According to the above-mentioned X-ray CT apparatus described in (7), a position guide index or an area guide index for selecting the interested area is shown on the first X-ray sectional image displayed on the display means and the interested area is selected by selecting operation of the position guide index or movement operation of the area guide index.

In this X-ray CT apparatus, the imaging interested area is selected by executing selection of the position guide index displayed on the first X-ray sectional image in the region to be imaged or by arranging the movement of the area guide index, so that the selection becomes easy using the position guide index or the area guide index.

(13) According to the above-mentioned X-ray CT apparatus described in (7) or (12), the interested area selection means is constructed so as to be able to display a diagram of the imaging region corresponding to the first X-ray sectional image and the interested area index movable on the diagram displayed on the display means, and wherein the interested area to be selected for the X-ray CT is constructed so as to be able to be specified by moving operation or selecting operation of the interested area index on the diagram shown.

According to the X-ray CT apparatus, the selection of the imaging interested area is done by moving the imaging interested area index displayed on the curved plane X-ray sectional image to the region to be imaged, so that the selection becomes easy using the imaging interested area index. The imaging interested area index may be one imitating the actual imaging interested area or may be a mouse pointer (arrow or cross) which is usually used as a positioning means on the display of the computer.

(14) According to the above-mentioned X-ray CT apparatus described in (1)-(13), the two-dimensional X-ray imaging sensor is comprised of any one of CdTe, MOS, CCD, XII, XICCD, photo diode array, or the like.

The kinds of the two-dimensional X-ray sensor are specifically described in order to achieve the effects of the present invention, so that the X-ray CT apparatus achieving the effects in (1)-(6) is easily constructed.

(15) According to the above-mentioned X-ray CT apparatus described in (1)-(14), wherein the start and the termination angles of the X-ray circulating radiation are set in such appropriate position or angle as for a patient to easily come in and out of the object holding means corresponding to the first and the second X-ray tomography, respectively.

(16) According to the above-mentioned X-ray CT apparatus described in (1)-(15), an X-ray beam switching means is provided for switching the shape of X-ray beam radiated from the X-ray generator in the first X-ray tomography and the shape of X-ray beam radiated from the X-ray generator in the second X-ray tomography.

(17) According to the above-mentioned X-ray CT apparatus described in (1)-(9) and (11)-(16), the curved plane X-ray tomography is executed for obtaining dental panoramic image or curved sectional X-ray image for use in otolaryngology.

(18) According to the above-mentioned X-ray CT apparatus described in (1)-(17), the X-ray computed tomography apparatus is comprised of a sectional image link means for subdividing in advance a second X-ray sectional image obtained by the second X-ray tomography into an assembly of X-ray sectional image comprised of plural X-ray sectional images cut out at a fixed interval at least in one direction of the three dimensional directions and for linking each X-ray sectional image in the assembly of the X-ray sectional images as the second X-ray sectional image to first X-ray sectional image obtained by the first X-ray tomography corresponding to the imaging region. The X-ray computed tomography apparatus is further comprised of an image recording means for storing together with each positional information the first X-ray sectional image and the second X-ray sectional image, each linked to the corresponding information, and a corresponding image calling means for invoking the linked corresponding X-ray sectional image when at least one of the first X-ray sectional image and the second X-ray sectional image stored in the image recording means is read out and is shown on the display means.

(19) According to the above-mentioned X-ray CT apparatus described in (18), the second X-ray sectional image subdivided into the assembly of plural X-ray sectional images is capable of being sequentially reproduced and displayed at least in one direction of three dimensional directions by moving operation of a cursor on the display means, and the linked corresponding X-ray sectional image is invoked from the corresponding image calling means when at least one of the first X-ray sectional image and the second X-ray sectional image stored in the image recording means is read out and shown on the display means.

Invoking of the corresponding X-ray sectional image is sassily done by operating a cursor.

(20) According to the above-mentioned X-ray CT apparatus described in (18)-(19), the first X-ray sectional image is a dental panoramic X-ray image.

(21) According to the above-mentioned X-ray CT apparatus described in (18)-(20), the X-ray sectional image corresponding to the first X-ray sectional image and/or the second X-ray sectional image are/is read out to be displayed on a part of the display means, when at least one of the first X-ray sectional image and the second X-ray sectional image stored in the image recording means is read out and displayed on the display means.

(22) According to the above-mentioned X-ray CT apparatus described in (1)-(21), the object holding means is movable in an axial direction of the X-ray rotary axis as well as in a vertical direction to the X-ray rotary axis.

BRIEF DESCRIPTION OF DRAWINGS

FIG. 6a shows a conceptual view of a flat plane X-ray tomography, FIG. 6b exemplifies an obtained flat plane sectional image, FIG. 6c exemplifies a CT image obtained at the X-ray rotary center selected in FIG. 6b.

BEST MODE FOR CARRYING OUT THE INVENTION

Now the preferred embodiment of the present invention is explained referring to the attached drawings.

Figure 1:
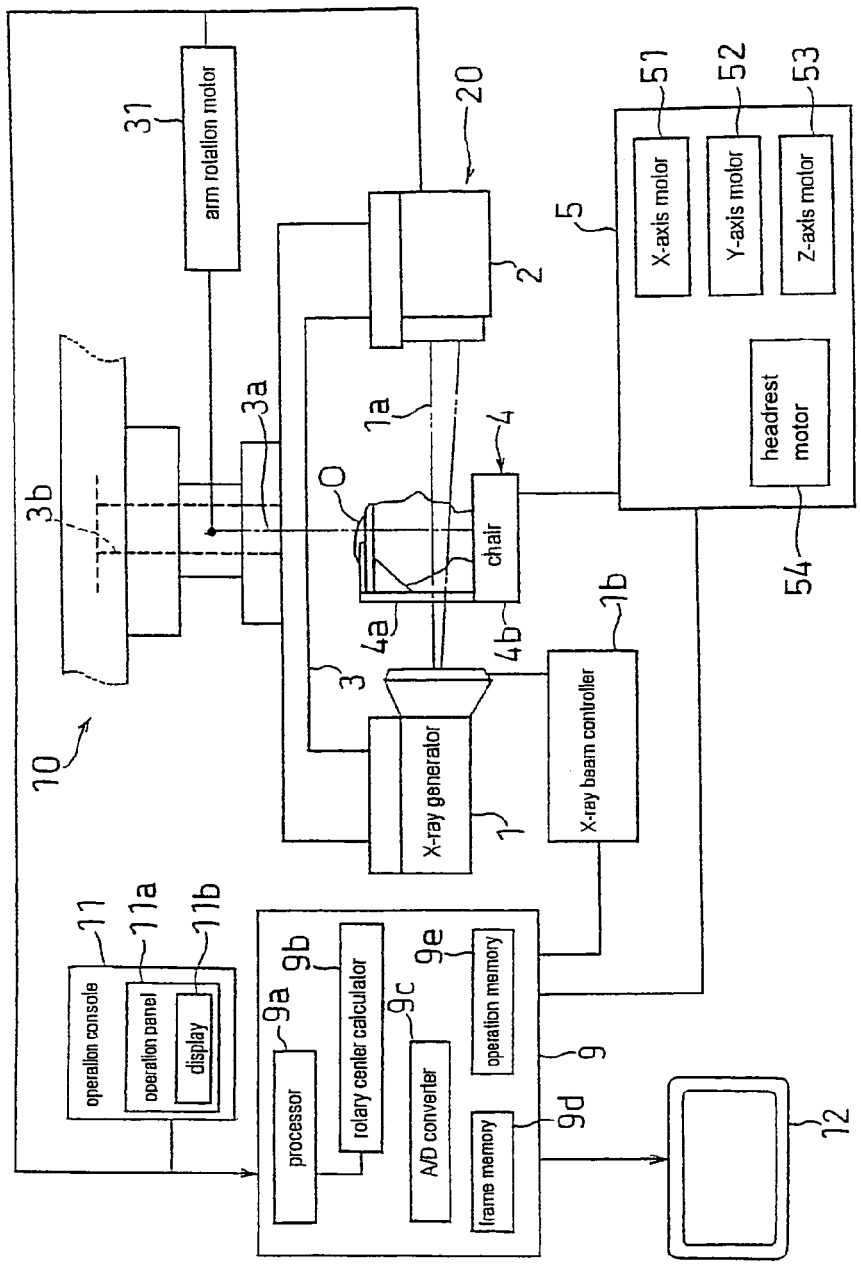
FIG. 1 shows an entire construction of one embodiment of the X-ray CT apparatus of the present invention.

FIG. 1 shows an entire construction of one embodiment of the X-ray CT apparatus of the present invention.

The X-ray CT apparatus 20 is comprised of a rotary arm 3 suspending an X-ray generator 1 and a two-dimensional X-ray image sensor 2 so as to face each other, an object holding means 4 for fixing an object, an object moving means 5 for horizontally moving the object holding means 4, an image processing means 9 controlling the apparatus entirely, a main frame 10, and an operation panel 11 with a display means 11b for simply showing an operational guide of the apparatus 20 and with an operation panel 11a for operating according to the display on the display means 11b.

In this embodiment, the rotary arm 3 is constructed as an X-ray radiation means and the X-ray generator 1 has an X-ray beam controller 1b for controlling the energy of generated X-ray beams so as to radiate X-ray conical beam with a predetermined beam width.

The two-dimensional X-ray image sensor 2 receives and detects the X-ray radiated from the X-ray generator 1 and transmitted through the object and outputs the X-ray transmitted image data as analog electric data or as digital data in case of having an A/D converter itself. Two-dimensional X-ray image sensor such as a cadmium telluride detector (CdTe) and a MOS sensor, a CCD image sensor which is a combination of a scintillator, a glass fiber, and the CCD, XII, XICCD, and photo diode array may be used. In this case, XII is used to output analog data.

In the XII, X-ray runs into a scintillator layer provided on the surface thereof is converted into a visible light, which is converted into electron to be electrically intensified by a photoelectric converter and the electron is converted to a visible light by a fluorescent material to be imaged by a two dimensionally arranged CCD camera (solid-state image sensing device) through a lens.

The two-dimensional image sensor is expensive and only a small one is commercialized. If a two-dimensional image sensor capable of detecting the object's head is used, X-ray imaging can be done regardless of a local region in case of CT. However, if X-ray CT is executed in the light of minimizing the X-ray exposure, it is necessary to radiate X-ray only on an imaging interested area. In such a case, the X-ray radiation area is minimized by means of the X-ray beam controller 1b which defines the shape of the X-ray beam radiated from the X-ray generator 1.

The rotary arm 3 is designed such that the X-ray rotary center 3a does not move into X, Y and Z directions, namely in horizontal or vertical direction, and an arm rotation motor 31 is only provided so as to turn the rotary arm 3 at a constant velocity or a variable velocity around the X-ray rotary center 3a.

The X-ray rotary center 3a of the rotary arm 3, namely a rotary axis, is provided vertically and the rotary arm 3 turns horizontally to locally irradiate conical X-ray beam 1a horizontally, thereby enabling to construct a vertical apparatus with a small occupied area.

The arm rotation motor 31 constructs a rotary drive means of the rotary arm 3. Any motors which can control the rotary speed and rotary position of the rotary arm 3 can be used, for example, a servo motor and a pulse motor. The motor is directly connected with an axis to the X-ray rotary center 3a of the rotary arm 3.

Accordingly, the rotary arm 3 is turned around the rotary center 3a and the rotational position is known along a time axis, thereby being convenient for timely taking out the X-ray transmitted image by means of the two-dimensional X-ray imaging device 2 and enabling X-ray CT effectively without causing deflection.

A hollow part 3b is provided for the rotary center 3a of the rotary arm 3. It is required to make a hollow part for all the members provided on the rotary center 3a in order to have such a hollow part 3b. For this purpose, a servo motor with a hollow axis can be used as an arm rotation motor 31.

The hollow part 3b is provided to arrange connection wires between the X-ray generator 1 and the X-ray imaging device 2 which are suspended from the rotary arm 3, the operation console 11 of the main frame 10, and the image processing means 9.

The method for arranging wires becomes a problem in order to provide an electric wiring for rotating members. If the connection wire is thus arranged through the X-ray rotary center 3a of the rotary arm 3, affection caused by rotation such as twist can be minimized and a preferable effect such as a beautiful appearance can be obtained.

The object holding means 4 is provided with a headrest 4a for holding an object O (a patient's head is used as an example here) and a chair 4b on which a patient sits for supporting the headrest 4a so as to be vertically movable.

The object holding means 4 is comprised of an X-axis motor 51 for moving the object holding means 4 in right and left direction, a Y-axis motor 52 for moving in back and forth direction, a Z-axis motor 53 for moving in up and down direction, and an object moving means 5 having a headrest motor 54 for moving the headrest 4a up and down relative to the chair 4b. These motors 51, 52, 53, 54 are constructed with a servo motor or a pulse motor.

The object O sits on the chair 4b with its head fixed by the head fixing means 4a and calibration is carried out so as to conform the imaging reference point of the object O and the imaging reference point of X-ray imaging by means of the object moving means 5. In case of a curved plane X-ray tomography, the object O is moved along a well-known orbit for a curved plane X-ray tomography during circulating radiation of X-ray. In case of CT, the X-ray rotary center 3a of the rotary arm 3 is conformed to the imaging interested area inside of the object O, namely the center of the imaging interested area when seen from a rotary axis direction of the X-ray rotary axis 3a.

According to the object holding means 4, a patient sits on the chair 4b with his head fixed with the headrest to radiograph the head as an object, thereby being utilized preferably as a vertical imaging apparatus.

In case of a horizontal type apparatus, the object holding means 4 becomes a bed type for horizontally supporting a bed-ridden patient and the object moving means 5 moves the bed in X, Y, or Z direction. Further in case of a horizontal type, the rotary arm 3 may be turned or a gantry may be provided in which the axial direction of the rotary axis of circulating X-ray radiation becomes horizontal, unlike vertical in a vertical apparatus.

The image processing means 9 has an operation processing means 9a constructed with an operation processor operable at high speed for image process analysis, and a rotary center position calculation means 9b as one function of the operation processing means 9a, an A/D converter 9c, a frame memory 9d, and an operation memory 9e.

Display selection means 12 is comprised of for example a personal computer to display a curved plane X-ray sectional image or an X-ray sectional image obtained by X-ray CT and to specify or select the position of a specific portion on the displayed curved plane X-ray sectional image.

The display selection means 12 also has a communication function to transmit data accumulated via a public phone line and so on, specifically a curved plane X-ray sectional image obtained by the X-ray CT apparatus 20 or a sectional image obtained by X-ray CT, to other apparatus, and to receive required data and images from other apparatus. Further, the display selection means 12 is provided with an external recording medium reproducer to record and store the above-mentioned data and the X-ray sectional images on a curved plane or a flat plane and the X-ray sectional image obtained by X-ray CT in a floppy disk, MO, DVD, CDR, CDRW and the like.

The image processing device 9 constructed as mentioned above is connected with the X-ray generator 1, the two-dimensional X-ray imaging sensor 2, each motor 31, 51, 52, 53, 54, the operation console 11 and the display selection means 12 respectively to process data sent from these devices, thereby executing control.

More specifically, the image data received from the two-dimensional X-ray imaging device 2 is converted into digital signals by the A/D converter 9c and the digitalized image data are stored in the frame memory 9d. Plural image data in the frame memory 9d are stored in the operation memory 9e and a predetermined operation for producing several X-ray sectional images is executed by the operation processing means 9a according to an imaging mode such as a curved plane X-ray tomography, a flat plane X-ray tomography, and an X-ray CT. Or a three-dimensional X-ray absorption coefficient on the imaging interested area is calculated. Several images are reconstructed from thus obtained three-dimensional X-ray absorption coefficient to be shown on the display selection means 12 or are stored in an external memory means (not shown).

The image processing device 9 controls the X-ray beam controller 1b, motors 31, 51, 52, 53, 54 by the operation processing means 9a so that the conical X-ray beam radiation from the X-ray generator 1, the rotation of the rotary arm 3 and the movement of the object moving means 5 corresponding to the rotation are controlled.

The X-ray beam controller 1b controls to vary the shape of the X-ray beam radiated from the X-ray generator 1 to the two-dimensional X-ray imaging device 2. For example, the beam is long in case of the first X-ray tomography such as a curved plane X-ray tomography, and is rectangular in case of CT being the second X-ray tomography.

If the light receiving area of the two-dimensional X-ray imaging device 2 is small relative to Z direction, imaging is repeated by changing the height of the object holding means 4 by means of the Z-axis motor 53 to patch the obtained data.

Figure 2:
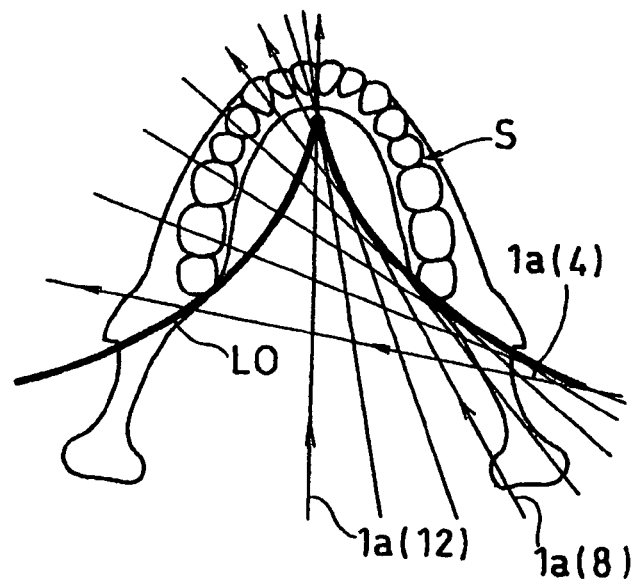
FIG. 2a and FIG. 2b conceptually explain a curved plane X-ray tomography according to the X-ray CT apparatus of the present invention.
Figure 2:
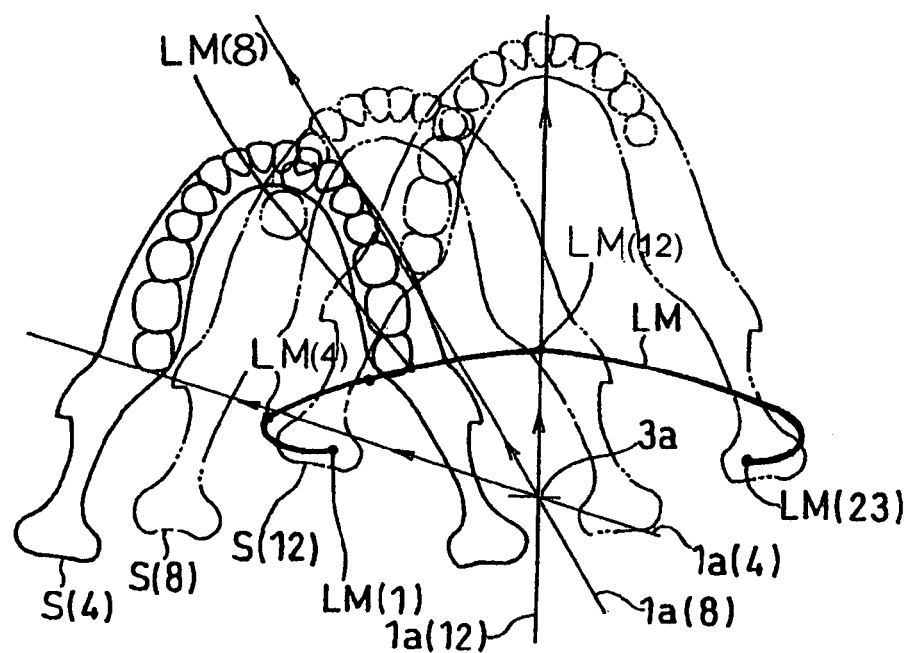

FIG. 2a and FIG. 2b conceptually explain a dental panoramic radiography according to the X-ray CT apparatus of the present invention. The parts already explained have the same reference numerals and their explanations are omitted.

In FIG. 2a, according to a curved plane X-ray tomography by a prior dental panoramic X-ray radiography, the orbit of X-ray beam 1a is shown when conical X-ray beam 1a is radiated on a dental arch S being an object while the X-ray rotary center 3a of the rotary arm 3 is moved, thereby forming an envelope curve LO of the X-ray beam 1a.

On the other hand, FIG. 2b shows a curved plane X-ray tomography by a dental panoramic radiography using the X-ray CT apparatus of the present invention.

The object holding means 4 on which a patient sits is moved corresponding to the rotary angle of the rotary arm 3 while the X-ray rotary center 3a of the rotary arm 3 is fixed, so that the dental arch S is moved along the panoramic X-ray image forming orbit LM and the X-ray beam 1a is radiated on the dental arch S.

In FIG. 2a, the X-ray beam 1a(4) is the X-ray beam selected at the forth time, the X-ray beam 1a(8) is the X-ray beam selected at the eighth time, and the X-ray beam 1a(12) is the X-ray beam selected at the twelfth time. In FIG. 2b the reference point of the dental arch S is positioned on the points LM(4), LM(8) and LM(12) on the panoramic X-ray image forming orbit LM respectively in order that the same X-ray beams 1a(4), (8), (12) are radiated. The corresponding dental arch S is shown as S(4), S(8), S(12) respectively.

Comparing FIG. 2a and FIG. 2b, it is understood that the X-ray beam 1a is radiated on the dental arch S in FIG. 2b like FIG. 2a.

In a curved plane X-ray tomography with the apparatus of the present invention, the center of the orbit of the X-ray circulating radiation is fixed, so that deflection of the rotary center is not caused and accuracy of X-ray CT is not deteriorated by the deflection. Further, the object is moved along the panoramic X-ray image forming orbit, so that the obtained X-ray transmitted images are patched as they are to obtain the panoramic X-ray image of a dental arch like a prior art without arranging the pace of expansion or without executing time-consuming back projection.

The first X-ray tomography is a method in which a sectional image plane with a predetermined thickness is supposed for the object and X-ray is radiated such that the X-ray transmitted image of the object is to be projected from different directions substantially within vertical area on the supposed sectional image plane. Thus obtained image is called as the first X-ray sectional image. In the field of dentistry, when the object is a dental arch and the predetermined sectional image plane is a sectional image plane of a curved plane on the dental arch, such a method is referred to a dental panoramic radiography, and thus obtained image is a dental panoramic X-ray image. Radiography for obtaining a curved plane X-ray sectional image of temporomandibular joint and a curved plane X-ray tomography of auditory ossicle in the field of otolaryngology are included.

Further, the image obtained by the first X-ray tomography may be obtained by executing time delay integration (TDI) on the transmitted image detected by the two-dimensional image sensor.

Still further, the first X-ray tomography includes a flat plane X-ray tomography such as a cross section radiography or a tangential radiography for obtaining the flat plane sectional image with a predetermined thickness which is orthogonal to the dental arch or is along the tangential direction of the dental arch.

As mentioned above, the first X-ray tomography is for imaging the X-ray sectional plane with a thickness corresponding to the thickness of the imaging object such as a tooth, a dental arch, a temporomandibular joint, an auditory ossicle. In a dental panoramic radiography, the thickness is different between a front tooth and a cheek tooth, namely the sectional thickness of the front tooth is small and that of the cheek tooth is large. The thickness of flat plane section is generally the same.

Figure 23:
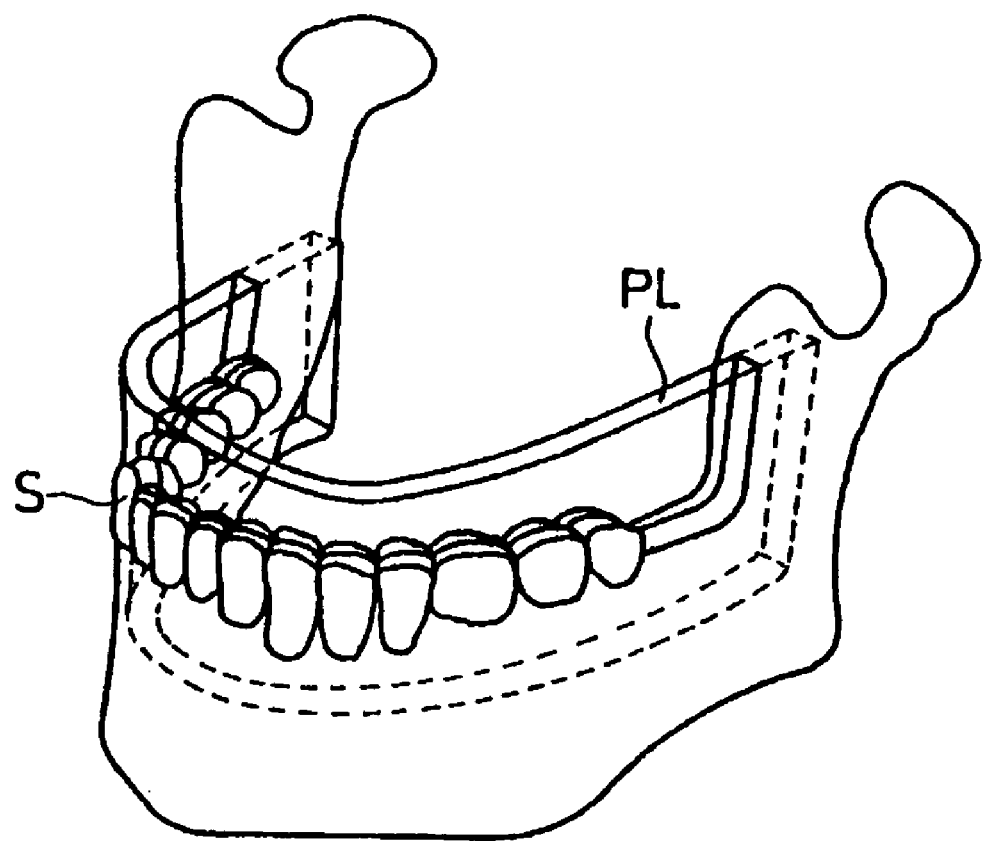
FIG. 23 is an image of a curved plane which is an imaging target in order to conceptually understand a dental panoramic X-ray radiography.

The curved section PL is shown as an image in FIG. 23 in order to understand the above-mentioned concept of a dental panoramic radiography.

Contrary, CT on an image interested area of an object is referred to the second X-ray tomography.

Figure 3:
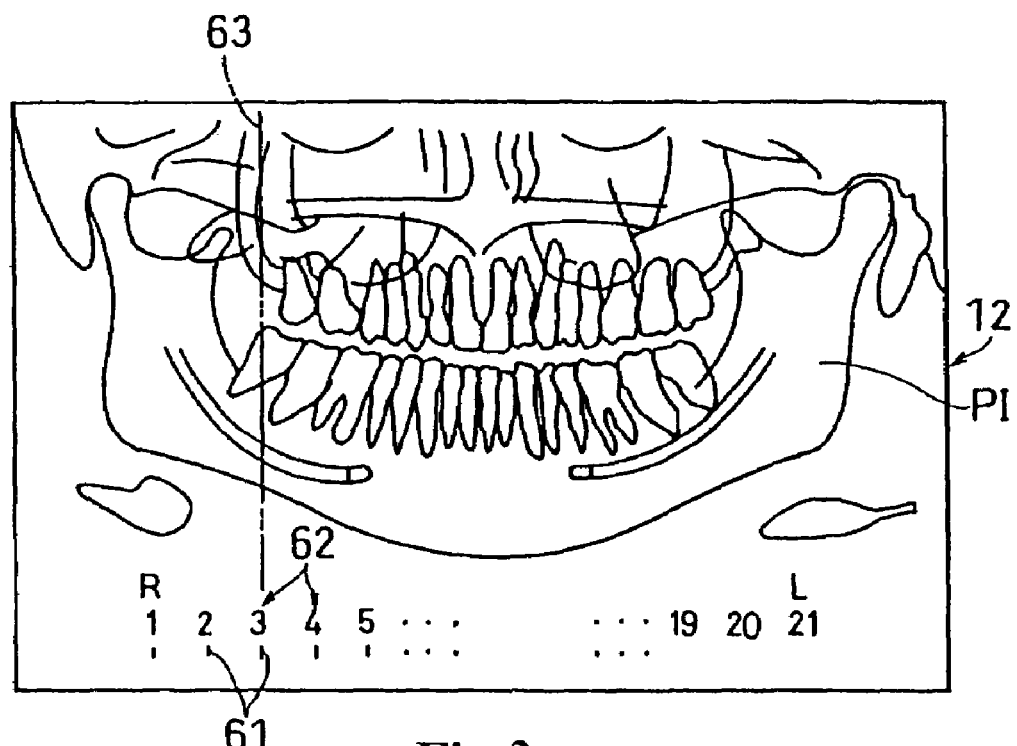
FIG. 3a and FIG. 3b conceptually explain selection of an imaging interested area using a curved plane X-ray sectional image obtained by the X-ray CT apparatus of the present invention.
Figure 3:
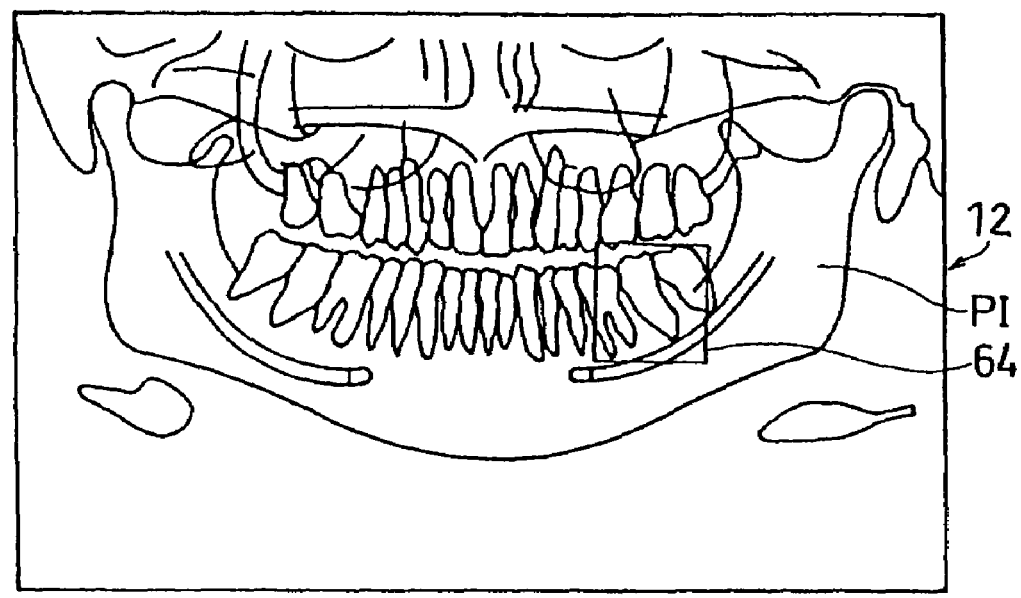
Figure 4:
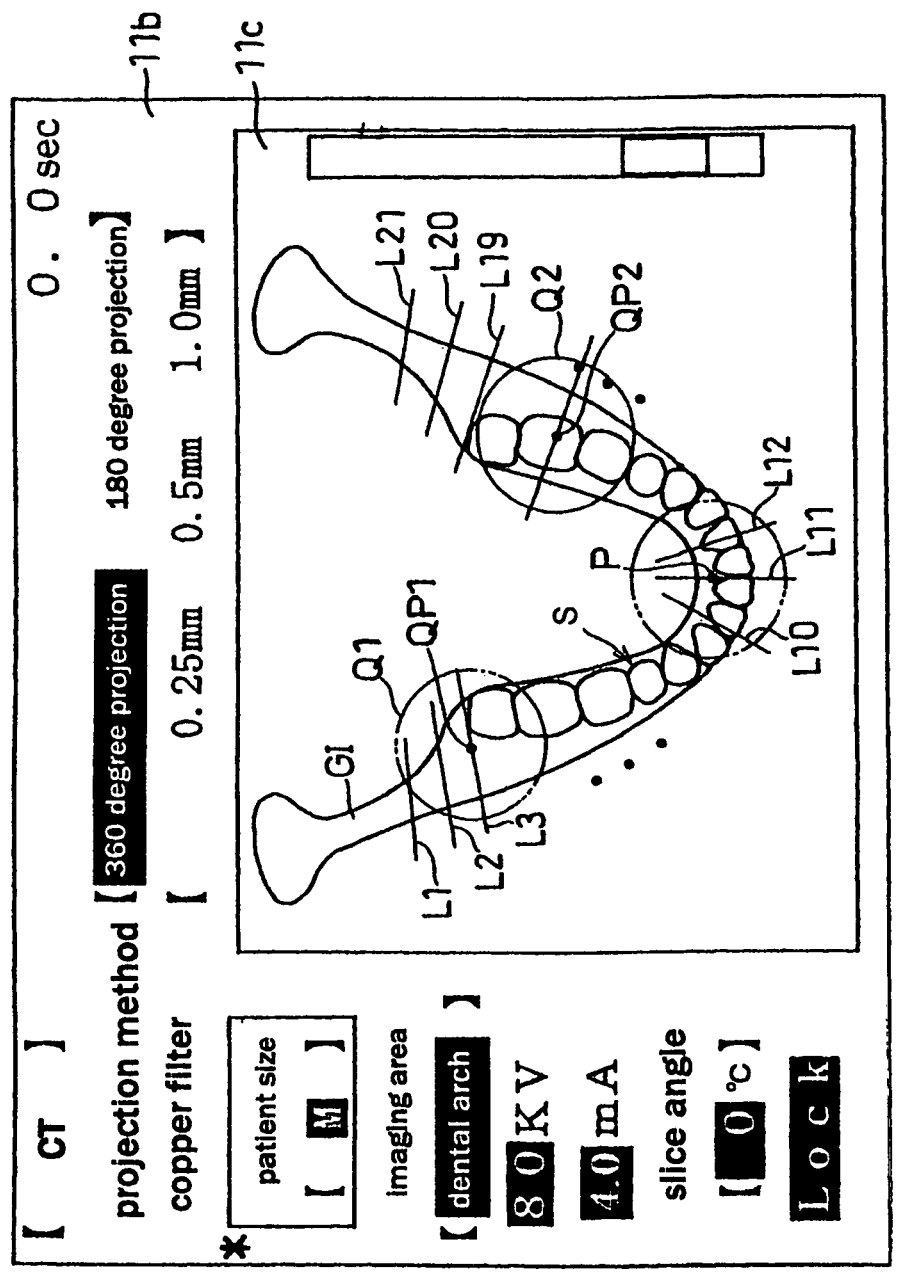
FIG. 4 conceptually shows a rotary center position calculated by the imaging interested area selected as shown in FIG. 3.

FIG. 3a and FIG. 3b conceptually explain selection of an imaging interested area using the curved plane X-ray sectional image obtained by the X-ray CT apparatus of the present invention. FIG.4 conceptually shows a rotary center position calculated by the imaging interested area selected in FIG. 3.

In FIG. 3a and FIG. 3b, the curved plane X-ray sectional image PI obtained by the panoramic radiography for a dental jaw as an object as shown in FIG. 2b is displayed on a display selection means 12.

In FIG. 3a, the reference numeral 61 is a guide point calculated by the rotary angle of the rotary arm 3 which is obtained by the curved plane X-ray tomography on the dental jaw. The guide point is a point for dividing the dental jaw including the dental arch at an even interval and becomes a guide for determining a coordinate of the position along the dental arch on the image of the entire dental jaw.

A guide number 62 is allotted in order on each guide point 61 from the right(R) to the left (L) when the dental jaw is seen from the object and twenty one guide points 61 are shown for the entire dental jaw.

These guide points 61 and the guide numbers 62 are index for guiding the position for selecting the imaging interested area of a local X-ray CT on the curved plane X-ray sectional image PI and they are called as a position guide index, respectively.

In FIG. 3b, the position guide indexes like FIG. 3a are not shown, instead an area guide index 64 is displayed for diagrammatically showing the imaging interested area of a local X-ray CT.

The area guide index 64 shows a possible imaging area indicating the area for CT. When the sectional image of conical X-ray beam for X-ray CT is rectangular, the index 64 needs to be rectangular, and when the section is circular, the index 64 is also required to be circular.

FIG. 4 shows an image shown on a display 11b of the X-ray CT apparatus 20 in which a dental jaw model GI which is a diagram of a dental jaw corresponding to the curved plane X-ray sectional image PI in FIG. 3 is displayed on the model display 11c in addition to several operation guides.

On the model GI, the reference numerals L1, L2, ... L20, and L21 are guide lines correspond to the guide points 61 in FIG. 3a, the direction of the guide lines L1 corresponds to the rotary angle of the rotary arm 3 and also corresponds to the direction of the X-ray beam 1 a radiated from the X-ray generator 1 to the two dimensional X-ray image sensor 2.

The reference numeral SI is a dental arch model shown on the dental jaw model GI, and the reference numeral P refers to an imaging reference point of the X-ray CT apparatus 20.

The selection of the imaging interested area for CT is done by clicking the guide point 61 or by entering the guide number "3" on a keyboard when the imaging interested area is judged to be at guide number "3" of the guide point 61 as shown in FIG. 3a.

Correspondingly, a guideline 63 with two-dotted line is shown on the curved plane X-ray sectional image PI.

The rotary center position calculation means 9b determines the position of the center QP1 of an imaging interested area index Qi in such a manner that the guideline L3 corresponding to the guide point 61 is selected as shown on the model display 11c in FIG. 4 the center QP1 of the imaging interested area index Qi with two-dotted line comes to the guide line L3 and the images of the dental jaw and the tooth around the guide line L3 are included.

The rotary center position calculation means 9b calculates movement data for horizontally moving the object holding means 4 in such a manner that the X-ray rotary center 3a conforms to the center QP1 of the imaging interested area index Q1, which is seen from the rotary axis direction of the X-ray rotary center 3a, according to the positional relation of the center and the imaging reference point P of the dental jaw. Thus obtained movement data is supplied to the object moving means 5.

Thus, the selection of the imaging interested area is done by selecting the position guide index in the area to be imaged among the indexes shown on the curved plane X-ray sectional image, so that the selection is facilitated using the position guide index as a guide.

Figure 5:
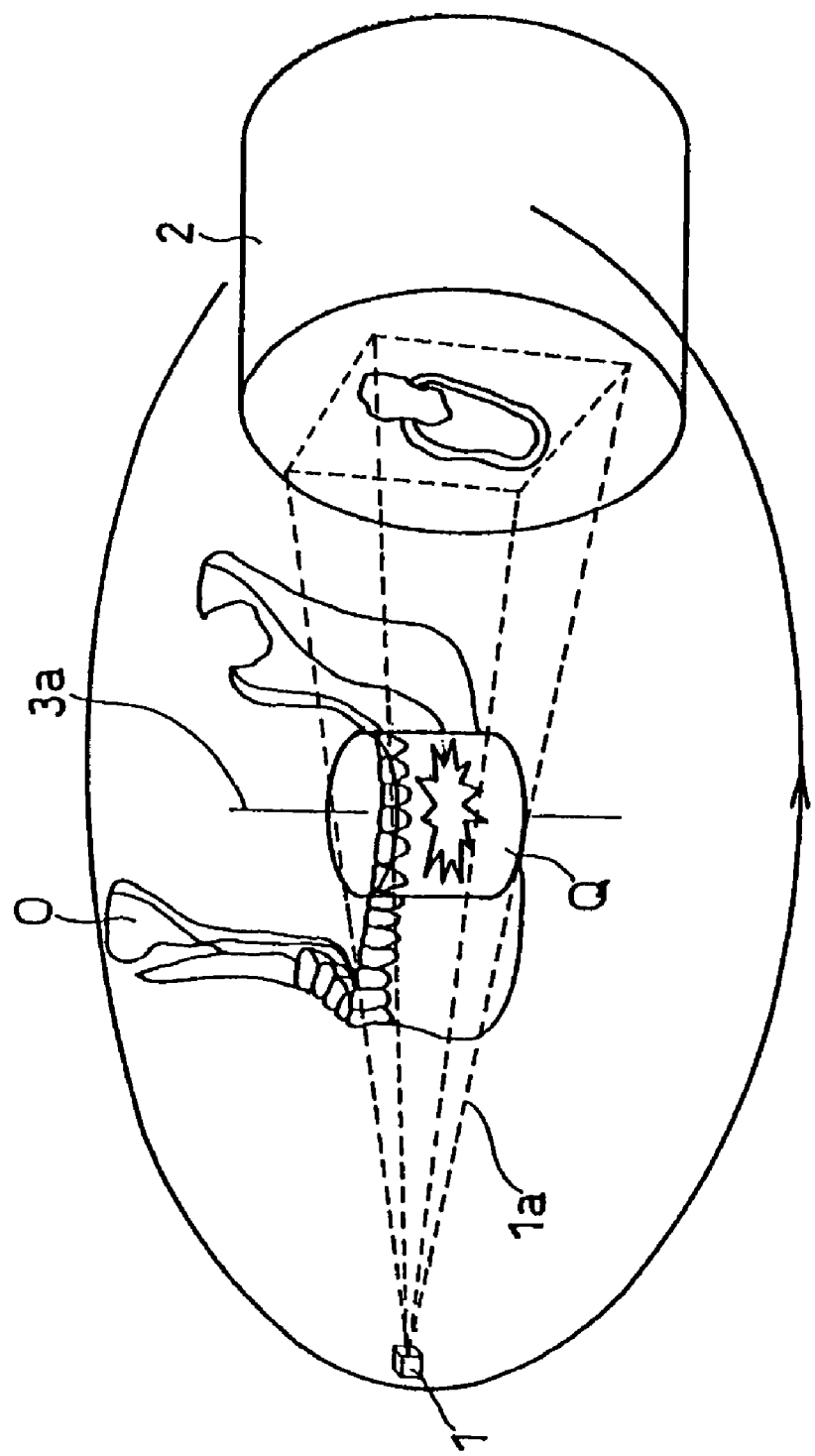
FIG. 5 conceptually shows a local X-ray CT executed by the X-ray CT apparatus of the present invention.

The imaging interested area index Q1 is the area which is always radiated by the conical X-ray beam 1a around the X-ray rotary center 3a when the conical X-ray beam 1a is radiated in a circulating manner with the center of the orbit of the X-ray circulating radiation is fixed as shown in FIG. 5 according to the X-ray CT apparatus of the present invention. When the sectional shape of the conical X-ray beam 1a is square, the index Q1 is cylindrical in three dimensional, the area guide index is rectangular on the side view like FIG. 3a and the imaging interested area index is circular on a plane view like FIG. 4.

The imaging interested area for CT may be selected by the method shown in FIG. 3b. Without using the guide point 61, the rectangular area guide index 64 is moved on the curved plane X-ray sectional image PI and the X-ray CT image is set on a required position, thereby selecting the imaging interested area.

In this embodiment, the area guide index 64 is at the left back teeth. Correspondingly, the rotary center position calculation means 9b calculates a movement data for horizontally moving the object holding means 4 in such a manner that the center QP2 of the displayed imaging interested area index Q2 is determined as shown in the model display 11c of FIG. 4, the X-ray rotary center 3a conforms to the center of the imaging interested area index, which is seen from the rotary axis direction of the X-ray rotary center 3a. Thus obtained movement data is supplied to the object moving means 5.

Thus, the selection of the imaging interested area is done by moving the area guide index shown on the curved plane X-ray sectional image, so that the selection is facilitated using the imaging interested area index as a guide.

Figure 24:
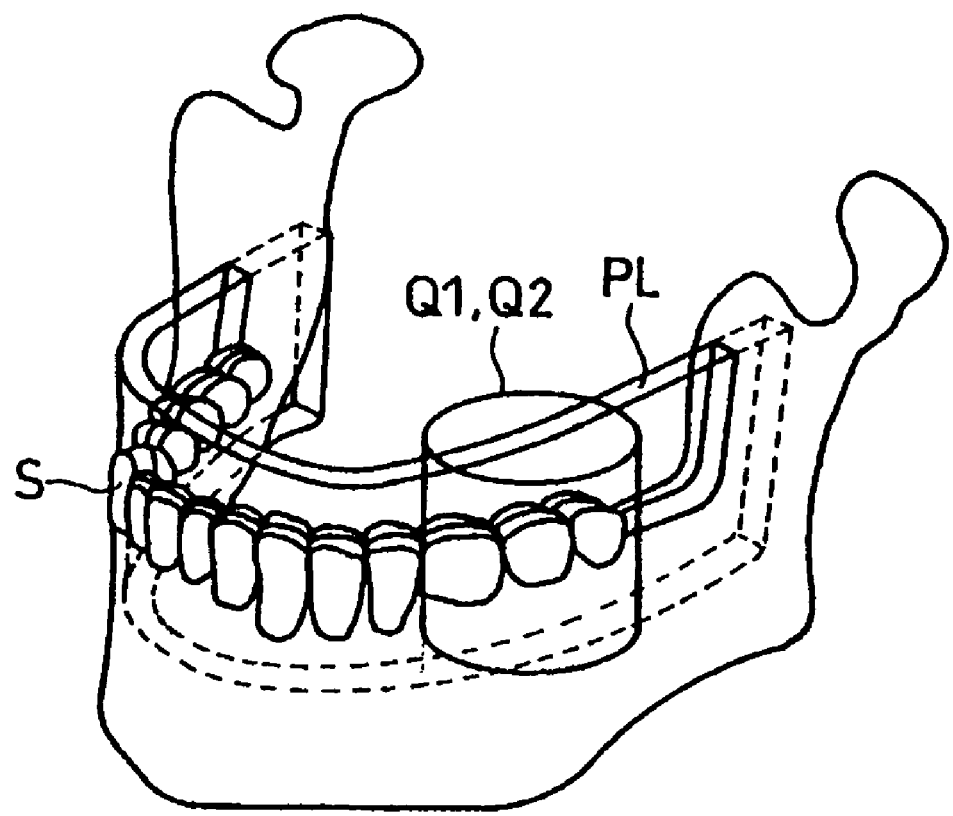
FIG. 24 is an image when the imaging interested area which is shown as an imaging interested area index Q1 or Q2 in FIG. 4 is overlapped on a curved plane PL on the curved plane X-ray sectional image.

FIG. 24 shows an image when the imaging interested area which is shown as the imaging interested area index Q1 or Q2 on the model display 11c in FIG. 4 is overlapped with a curved sectional plane PL being an imaging object which is also shown in FIG. 23 in order to understand the selection concept of the imaging interested area, which is an imaging object of X-ray CT, from the curved plane X-ray sectional image.

The position guide index may be both of the guide point and the guide number or either one of them. The area guide index or the imaging interested area index may be the shape like the actual imaging interested area as mentioned in this embodiment, or may be a mouse pointer (arrow or cross) which is usually used as a positioning means on the display of a computer. Or the position guide index and the area guide index may be shown at the same time.

In such a case, the time from starting the curved plane X-ray tomography to fixing the X-ray rotary center of the rotary arm 3 within the selected imaging interested area of the object is extremely short, thereby executing X-ray CT without imposing a burden on a patient while the object is held and fixed with the object holding means. As a result, the curved plane X-ray tomography and the X-ray CT can be skillfully linked each other.

Specifically, after the object O is set on the object holding means 4, it takes about 80 seconds as a standard till execution of curved plane X-ray tomography, display of the curved plane X-ray sectional image, selection of the imaging interested area, calculation of a fixing position of the X-ray rotary center and execution of X-ray CT.

The following advantages are skillfully combined: the X-ray CT apparatus 20 rapidly produces images by digital processing; the curved plane X-ray sectional image is produced in a short time by directly patching images in the X-ray CT apparatus 20; thus digitalized curved plane X-ray sectional image data includes a rotary angle data, so that by selecting the imaging interested area on the image, the horizontal position of the imaging interested area in the object is calculated from the rotary angle data corresponding to the imaging interested area and the statistical dimensional data of the object, and the movement data mentioned above is obtained.

In this embodiment, the center of the orbit of the X-ray circulating radiation is fixed at the center of the imaging interested area, which is seen from the rotary axis direction of the X-ray rotary center 3a and the radiation center axis of the conical x-ray beam passes the X-ray rotary center. However, the fixing method of the X-ray rotary center on the imaging interested are is not limited to such a method.

For example, if the imaging interested area is larger than the radiation width of the conical X-ray beam, the conical X-ray beam is radiated while the radiation center axis thereof is eccentric out of the X-ray rotary center, so that the conical X-ray beam can be radiated in a circulating manner on the entire area of the large imaging interested area. The phrase "the center of the orbit of the X-ray circulating radiation is fixed on the imaging interested area" in this specification includes such a case.

The operational guide shown on the display 11b of FIG. 4 other than the model display 11c is convenient as a guide for several operations for radiography.

The first tomography may include the blurred image on the area other than the objective imaging region and the second tomography may obtain the X-ray sectional image excluding the blurred image by means of a computed tomography in which a three-dimensional absorption coefficient data is computer processed for accurate diagnosis.

The X-ray absorption distribution information of the sectional area is digitally obtained relative to the X-ray sectional image in the interested area obtained by the second tomography and the X-ray sectional image excluding the images out of focus can be obtained by the X-ray absorption distribution information. Therefore, the X-ray sectional images other than the blurred image can be obtained for the tomography of the interested area which is often required to obtain an accurate X-ray sectional image, thereby contributing to an accurate diagnosis.

FIG. 5 conceptually shows a local X-ray CT executed by the X-ray CT apparatus of the present invention.

In a local X-ray CT executed by the X-ray CT apparatus of the present invention, conical X-ray beam 1a is locally radiated only on the imaging interested area Q of the object O, namely the conical X-ray beam 1a is always radiated only on the imaging interested area, while turning the rotary arm 3 suspending the X-ray generator 1 and the two-dimensional X-ray image sensor 2 so as to be faced each other.

Its radiography condition is: conical X-ray beam 1a including only the imaging interested area Q is generated from the X-ray generator 1, and the rotary arm 3 is turned while fixing the X-ray rotary center 3a on the center of the imaging interested area Q seen from the rotary axis direction of the X-ray rotary center 3a.

The actual size of the imaging interested area Q is fixed, for example, the diameter is 40 mm and the height is 30 mm, which is suitable for obtaining the X-ray image of a partial area of the dental jaw, however, the size is optionally selected.

The electric signal obtained on the two-dimensional X-ray image sensor 2 by such radiation is rendered to a digital processing and a back projection processing to obtain the three-dimensional X-ray absorption coefficient of the imaging interested area which is locally radiated, thereby obtaining an optional X-ray sectional image in the imaging interested area. Comparing to the prior art in which X-ray is radiated on the entire object, the X-ray exposure amount of the object is reduced into from a few tenth to a few hundredths by such a local radiation.

This method is based on an idea such that the X-ray transmitted image data is usually obtained for the area to which conical X-ray beam 1a is locally radiated, namely the imaging interested area, however, the conical X-ray beam 1a temporally transmits through the other parts of the object surrounding the imaging interested area Q accompanied with rotation comparing to the imaging interested area Q and its affect on the image data is only a little, so that the affect can be almost ignored in case of back projection.

When the difference of the X-ray absorption coefficient of the imaging interested area and that in the area therearound is large, for example, there is a tooth, bone, an implant and so on in the imaging interested area, the obtained curved plane X-ray sectional image can be an image with enough contrast emphasizing the tooth, the bone, and the implant against the soft tissue area therearound in order to diagnose the shape. Therefore, the X-ray image obtained by locally radiating the conical X-ray beam only on the imaging interested area can be practically used for actual diagnosis.

According to this X-ray CT apparatus of the present invention, the imaging interested area to be locally radiated is easily selected on the curved plane X-ray sectional image obtained by the curved plane x-ray tomography with the same apparatus and calculates the position of the X-ray rotary center is calculated based on the selection and to move the object. Therefore, X-ray CT can be executed effectively and speedy for the accurate imaging interested area, thereby preferably achieving the effect of local radiation.

The apparatus for executing X-ray CT by locally radiating X-ray only on the projection interested area is specifically referred to a local X-ray CT apparatus and its details are disclosed in JP-A-2000-139902.

Figure 6:
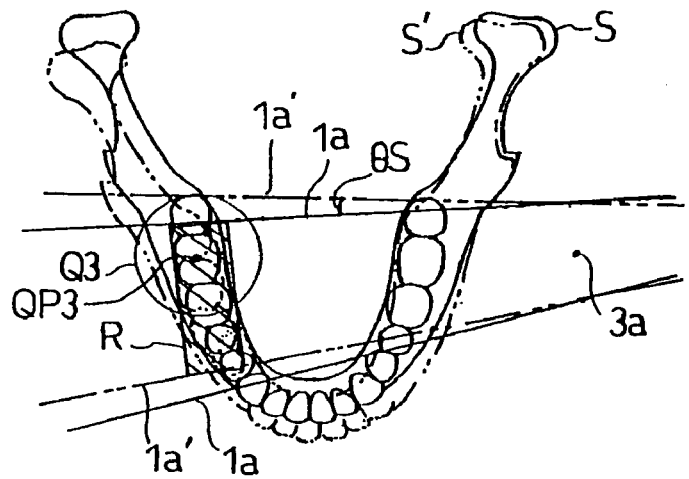
FIG. 6 conceptually shows link of a flat plane X-ray tomography and a CT according to the present invention.
Figure 6:
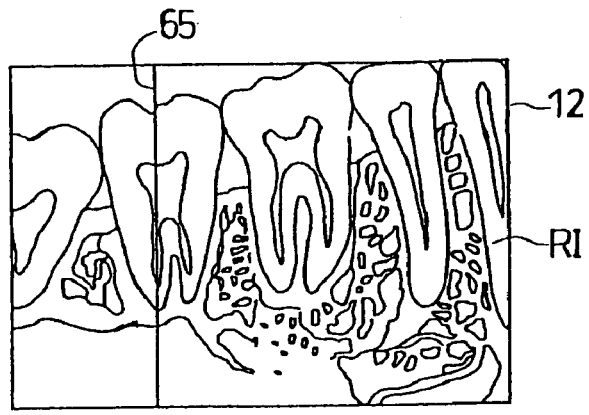
Figure 6:
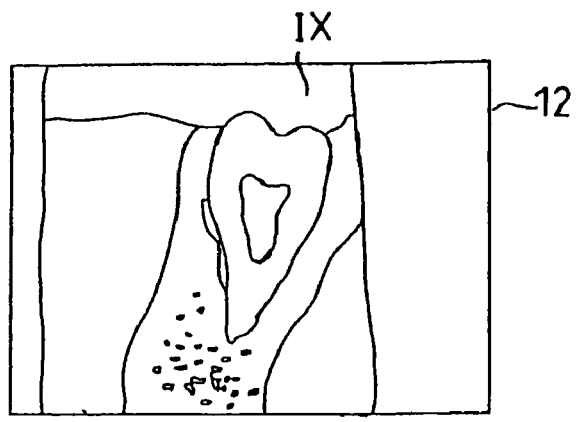

FIG. 6 conceptually shows link of a flat plane X-ray tomography and a CT according to the present invention, FIG. 6a shows a conceptual view of a flat plane X-ray tomography, FIG. 6b exemplifies an obtained flat plane X-ray sectional image, FIG. 6c exemplifies a CT image obtained at the X-ray rotary center selected in FIG. 6b.

In the flat plane X-ray tomography, a flat sectional plane R with a predetermined thickness is set at an optional position on the dental arch S being an object and X-ray beam 1a is radiated in a different angle within the vertical area to the flat sectional plane R.

Specifically, in case of circulating radiation, when the X-ray beam 1a is radiated in a circulating manner at a slight angle θs as shown in FIG. 6a, the X-ray rotary center 3a of the X-ray generator 1 and the two-dimensional X-ray image sensor 2 is positioned to radiate in a circulating manner the X-ray beam 1a in such a manner that the X-ray beam 1a always radiates the flat sectional plane R within substantial vertical area.

The X-ray beam 1a may be rotated at a slight angle θS such that the X-ray beam 1a (solid line) comes to the X-ray beam 1a' (imaginary line). Or without rotating the X-ray beam 1a, the dental arch S (solid line) being an object may be moved describing an arc to the dental arch S' (imaginary line) around the rotary center 3a of the X-ray beam 1a at the slight angle 6 S in an opposite direction. If the angle θS is quite small, the dental arch S may be linearly moved into a bowstring direction connecting both ends of the circular movement instead of moving the dental arch S so as to describe an arc.

According to the X-ray CT apparatus 20 of the present invention in which the X-ray generator 1 and the X-ray imaging means 2 are capable of turning around the fixed X-ray rotary center 3a and the object O is movable by the object moving means 5, circulation of the X-ray beams 1a or the circular or linear movement of the object is possible as the mentioned above.

The object may be turned at a slight angle θs by the object moving means 5, and the X-ray beam 1a may be radiated on the flat plane section R from a different angle.

X-ray beam 1a is thus radiated on the flat plane section R, a flat plane X-ray tomography which has little affect of the image other than the flat plane section R by optionally selecting and extracting from the obtained X-ray transmitted image, thereby obtaining the flat plane X-ray sectional image RI shown in FIG. 6b.

Such a principle of tomography is basically the same as that of a curved plane X-ray tomography of the X-ray imaging apparatus capable of reconstructing the received X-ray image as digital data as disclosed in JP-B-2-29329.

A projection interested area index line 65 achieving the same function as the imaging interested area index 64 in FIG. 3b is positioned at a desirable place (for example the place shown in FIG. 6b), so that the rotary center position calculation means 9b calculates the center QP3 of the projection interested area Q3 seen from the rotary axis direction of the X-ray rotary center 3a, like FIG. 4. Thus obtained center QP3 of the projection interested area Q3 is shown in FIG. 6a.

After calculating the position of the center QP3, CT is executed while fixing the X-ray rotary center 3a on the center QP3, a three-dimensional X-ray absorption coefficient of the projection interested area Q3 is obtained, and the image IX shown in FIG. 6c is obtained by reconstructing the coefficient.

In this embodiment, the time fro the start of flat plane X-ray tomography to when the center of the X-ray circulating radiation is fixed on the selected imaging interested area of the object is very short like the embodiment in FIG. 3 and FIG. 4, so that X-ray CT is executed while fixing the object on the object holding means without imposing a burden on the patient. Therefore, skillful link of the flat plane X-ray tommgraphy and the X-ray CT is possible.

Figure 7B:
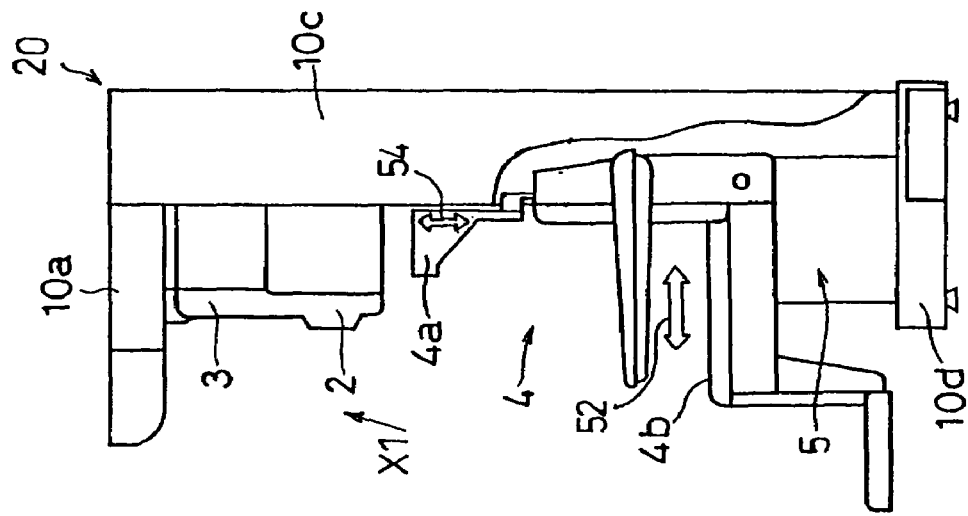
FIG. 7a is a front view of the X-ray CT apparatus of the present invention and FIG. 7b is its side view.
Figure 7A:
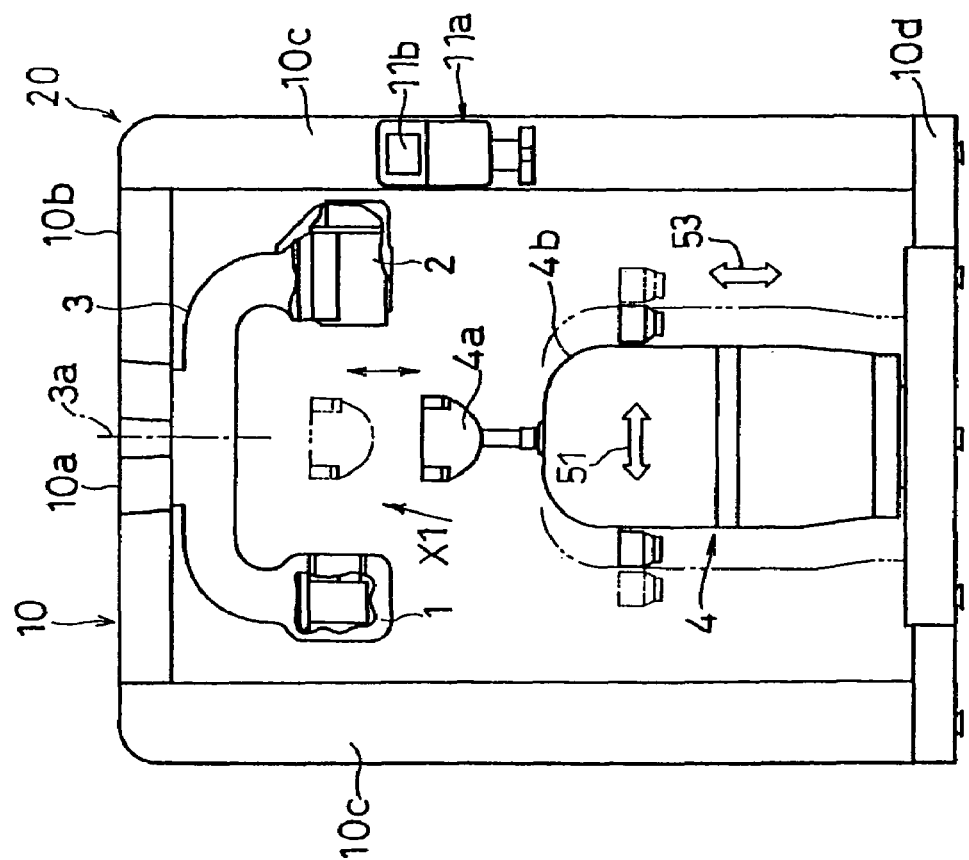

FIG. 7a is a front view of the X-ray CT apparatus of the present invention and FIG. 7b is its side view.

According to the X-ray CT apparatus 20, the X-ray generator 1, the two-dimensional X-ray imaging sensor (X-ray imaging device) 2, the rotary arm 3, the object holding means 4, the object moving means 5, and the operation panel 11a with the display 11b are provided for the main arm 10 as shown in the figure.

The display 11b is provided on the surface of a vertical beam 10c which is one of main frame 10 and on the operation panel 11a arranged where an operator easily uses the panel 11a while standing. The display 11b shows a dental jaw model and a guide display for operation.

Movement switch (not shown) is provided for the operation panel 11a to move the chair 4b side to side, back and forth or up and down by means of the object moving means 5. The object moving means 5 is also used to conform the reference position of radiography and an imaging reference point P (FIG. 4) of the object by means of the switch.

The main frame 10 is comprised of an arm 10a rotatably supporting the rotary arm 3, a cross beam 10b fixing the foundation of the arm 10a, a pair of vertical beams 10c supporting the cross beam 10b, and a base 10d on which a pair of vertical beams 10c are fixed and which is the foundation of the entire apparatus 20.

A highly rigid steel material is used for the members of the main frame 10 and braces and angular reinforcing members are appropriately used for resisting deformation so as not to vary the X-ray rotary center 3a of the rotary arm 3 during rotation.

The main frame 10 is constructed not to cause the rotary deflection of the rotary arm 3, so that it is applicable to the X-ray CT apparatus which requires no rotary deflection.

In this figure, the X-axis motor 51, the Y-axis motor 52, the Z-axis motor 53 and the backrest motor 54 comprises the object moving means 5 for moving the object holding means 4 for holding a patient, as explained referring to FIG. 1, and they are conceptually shown with outlined arrows with the same reference numerals.

Figure 8:
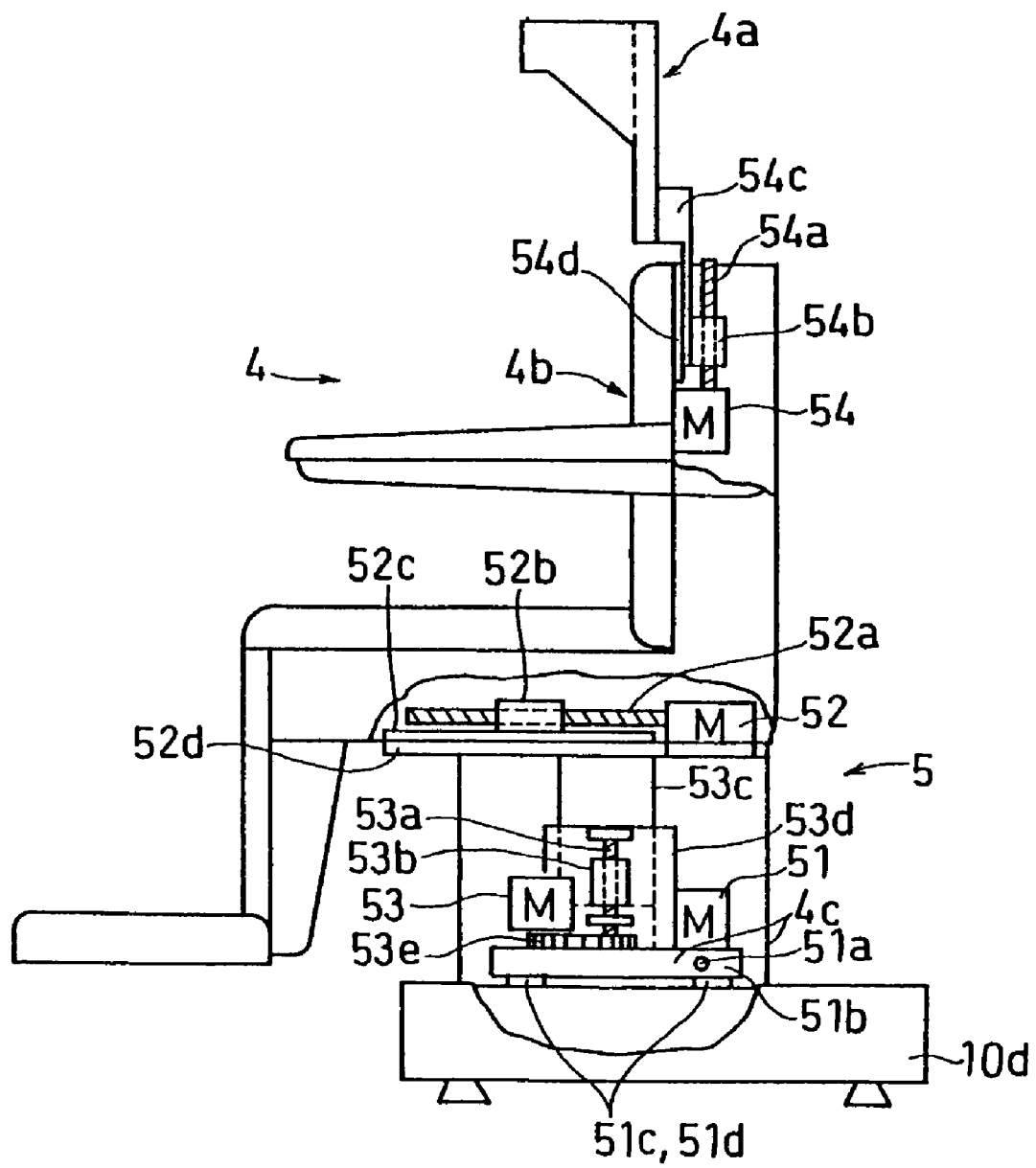
FIG. 8 shows an object moving means provided for the X-ray CT apparatus of the present invention.

FIG. 8 shows an object moving means provided for the X-ray CT apparatus of the present invention in which a part of the object holding means 4 in FIG. 7b is enlarged and shown as a partial broken view.

The object moving means 5 is provided in the object holding means 4 or at its periphery as shown in FIG. 8 and is comprised of the X-axis motor 51, the Y-axis motor 52, Z-axis motor 53 and the headrest motor 54, a ball screw 51a, 52a, 53a, 54a which is driven to be rotated by each motor, a female screw 51b, 52b, 53b, 54b which is engaged with each screw, a male rail 51c, 52c, 53c, 54c which is fixed by the male screw to be slid together, a female rail 51d, 52d, 53d, 54d for accurately sliding the male rail.

The X-axis motor 51, the ball screw 51a and the female rail 51d are fixed on the base 10d, the female screw 51b and the male rail 51c are fixed on a base 4c of the object holding means 4, and the object holding means 4 is moved in X direction (like an outline character 51 in FIG. 7, namely horizontal direction) relative to the base 10d by controlling the rotation and drive of the X-axis motor 51.

The Z-axis motor 53, the ball screw 53a and the female rail 53d are fixed on the base 4c side of the object holding means 4, the female screw 53b and the male rail 53c are fixed on the chair 4b, the chair 4b is moved in Z direction (like an outline character 53 in FIG. 7, namely up and down direction) relative to the base 4c by controlling rotation and drive of the Z-axis motor 53, so that the height of the object is controlled for the rotary arm 3.

In the Z direction, the rotary driving force is transmitted between the Z-axis motor 53 and the ball screw 53a by means of a timing belt 53e and a timing pulley (not shown) because of the limitation of the place, however, they may be directly connected if there is no limitation of place. As for the combination of the female rail 53d and the male rail 53c is such that a large caliber piston and cylinder are combined in order to reduce deflection of the chair 4b relative to the base 4c when the chair 4b is horizontally moved.

The Y-axis motor 52, the ball screw 52a and the female rail 52d are fixed on the male rail 53c moving up and down for the base 4c of the object holding means 4, the female screw 52b and the male rail 52c are fixed on the chair 4b, and the chair 4b is moved in Y direction (an outline arrow 52 in FIG. 7, namely back and forth direction) relative to the base 4c by controlling rotation and drive of the Y-axis motor 52.

The headrest motor 54, the ball screw 54a, the female rail 54d are fixed on the upper part of the chair 4b of the object holding means 4, the female screw 54b and the male rail 54c are fixed on the headrest 4a, and the headrest 4a is moved in Z direction (an outlined arrow 54 in FIG. 7, namely up and down direction) relative to the upper part of the chair 4b by controlling rotation and drive of the headrest motor 54, so that the up and down position of the headrest 4a can be arranged depending on the patient sitting on the chair 4b.

For moving the object holding means 4 in a vertical direction, the X direction moving means comprised of the X-axis motor 51 and so on and the Y direction moving means comprised of the Y-axis motor 52 and so on are used among the above-mentioned object holding means 5.

Generally known method using rails and ball screws is explained as a moving means of an X-axis, a Y-axis and a X-axis in above, however, a well known cross roller guide and a combination of a normal bearing and guide may be used as a guide means and a rack-and-pinion method or a normal screw ball may be used as a driving method. Any method capable of accurately positioning is preferable.

Figure 9:
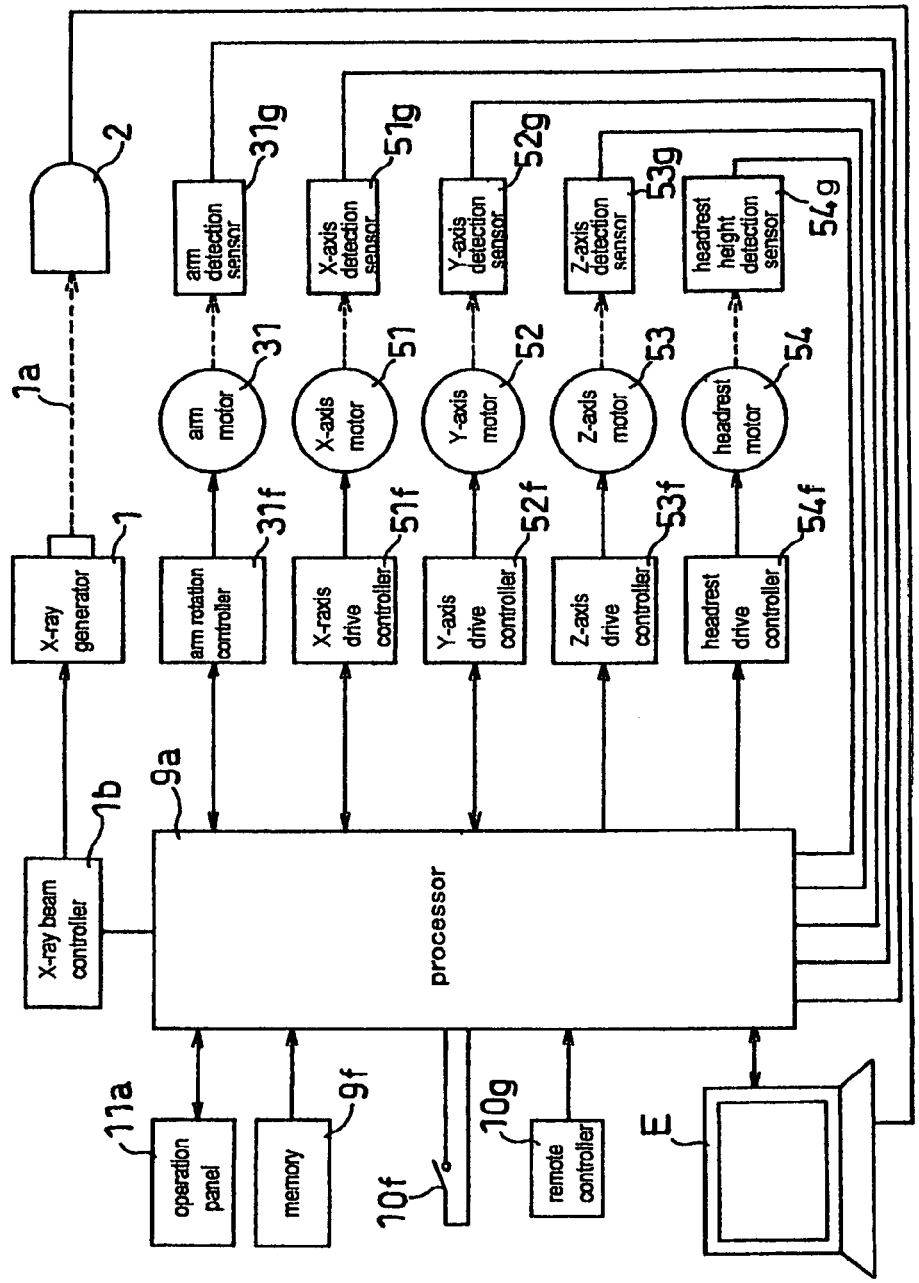
FIG. 9 is a control block diagram relating to a curved plane X-ray tomography according to the X-ray CT apparatus of the present invention.

FIG. 9 is a control block diagram relating to the first X-ray tomography such as a curved plane X-ray tomography according to the X-ray CT apparatus of the present invention.

FIG. 9 is a control block diagram in which control of circulating X-ray radiation and control for moving an object are extracted from the entire construction view of FIG. 1 to explain in more detail.

An arm rotation motor 31, the X-axis motor 51, the Y-axis motor 52, the Z-axis motor 53, the headrest motor 54 are connected to the operation processing means 9a via an arm rotation controller 31f, an X-axis drive controller 51f, a Y-axis drive controller 52f, Z-axis drive controller 53f and a headrest drive controller 54f which drives each motor, respectively.

The driven side such as a rotary arm 3 driven by the motors 31, 51, 52, 53, 54 is provided with an arm origin detection sensor 31g, an X-axis origin detection sensor 51g, a Y-axis origin detection sensor 52g, a Z-axis origin detection sensor 53g, and a headrest height detection sensor 54g and their outputs are connected to the operation processing means 9a.

The operation processing means 9a is connected with the operation panel 11a, a memory 9f storing control data or program, a radiation switch 10f being a starting switch of X-ray radiation and a remote controller 10g for remotely executing required operations.

Thus constructed operation processing means controls to radiate X-ray in a circulating manner and to move the object.

Figure 10:
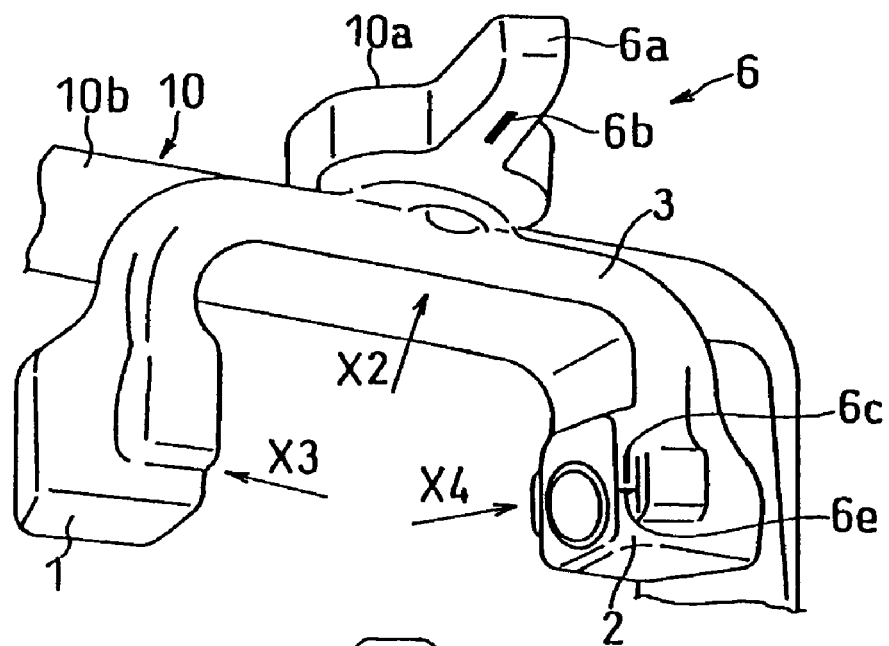
FIG. 10 is an explanatory view of a guide beam generation means according to the present invention.
Figure 10:
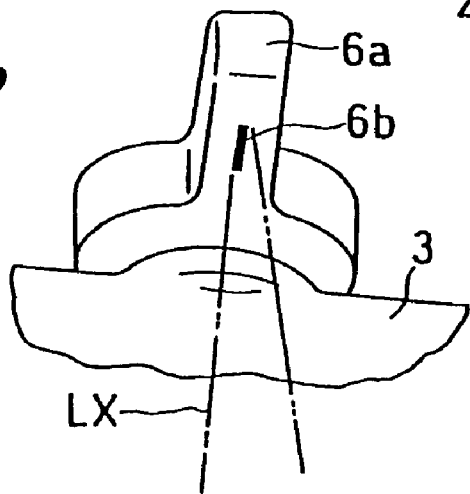
Figure 10:
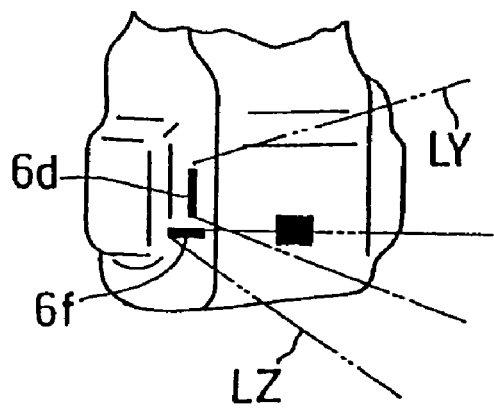
Figure 10:
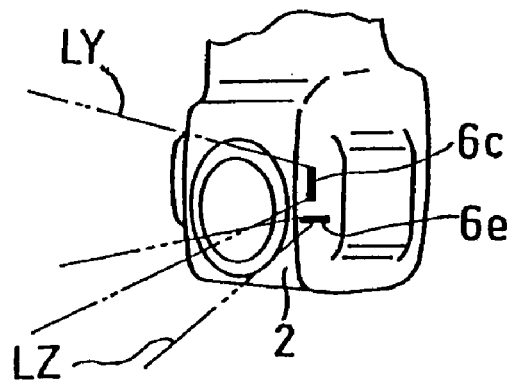

FIG. 10 is an explanatory view of a guide beam generation means according to the present invention. FIG. 10a is a fragmentary view in the direction X1 of FIG. 7, FIG. 10b is a fragmentary view in the direction X2 of FIG. 10a, FIG. 10c is a fragmentary view in the direction X3 of FIG. 10a, FIG. 10d is a fragmentary view in the direction X4 of FIG. 10a.

The guide beam generation means 6 is used for both the curved plane X-ray tomography and the X-ray CT of the X-ray CT apparatus 20, and is used for conforming the reference point P of the object and the reference point of radiography, which is inevitable before radiography.

The guide beam generation means 6 is comprised of a support body 6a extended from the arm 10a, a right and left guide beam generation means 6b provided for the support body 6a to radiate a right and left guide beam LX, a pair of back and forth guide beam generation means 6c, 6d provided for the X-ray generator 1 and the two-dimensional X-ray image sensor 2 respectively to radiate a back and forth guide beams LY, and a pair of guide beam generation means 6e, 6f provided for the X-ray generator 1 and the two-dimensional X-ray image sensor 2 respectively to radiate an up and down guide beam LZ.

Thus constructed guide beam generation means 6 can radiate the guide beam LX, LY, LZ as mentioned later referring to FIG. 11 and is functioned as a calibration means for conforming the imaging reference point P of the object and the reference point of radiography.

Beam generation means are provided in symmetrical in right and left for the back and forth guide beam LY and the up and down guide beam LZ because the guide beam is seen from the illuminating side but the guide beam is not seen because of the object from the opposite side if only one beam generation means is provided. Therefore, a pair of guide beam generation means 6c, 6d and 6e, 6f are designed such that radiating guide beams are conformed in an opposite manner.

Thus constructed guide beam is used as a calibration means, calibration can be executed without contacting with the object, and further, the guide beam itself becomes a guide for displaying the imaging interested area Q in the object on the surface of the object, so that the imaging interested area is easily understood.

FIG. 11a is a side view showing when an object is fixed to an object holding means and FIG. 11b is a perspective view showing how a calibration means is used.

As shown in FIG. 11a, the headrest 4a has a support portion 4aa detachably fixed on the male rail 54c provided at the upper part of the chair 4b of the object holding means 4 and a head fixing band 4ab provided for the support portion 4aa to fix and hold the object O which is a human head at an appropriate position.

The reference numerals LY, LZ refer to the back and forth guide beam, the up and down guide beam as shown in FIG. 10 and the right and left guide beam LX shown in FIG. 11b is not shown because FIG. 11a is a side view. FIG. 11b is a perspective view, so that all guide beams LX, LY, LZ are seen.

The guide beams LX, LY, LZ show the imaging reference point at the imaging apparatus side of the X-ray CT apparatus 20. When the guide beams LX, LY, LZ are designed to be positioned at the imaging reference point P of the object O, the reference point of radiography at the apparatus side and the imaging reference point P of the object O are conformed.

When the object holding means 4 is moved relative to the guide beams LX, LY, LZ by the object moving means 5, their relative position is varied to conform each guide beam LX, LY, LZ to the actual imaging reference pint P of the object O, thereby executing calibration.

As a substitute for the guide beam, a calibration means 6A comprised of a contactor as shown in FIG. 11a may be used. When the contactor 6A gets in contact with the imaging reference point P of the object O, the imaging reference point P of the object O and the reference point of radiography of the apparatus 20 are conformed, thus executing calibration.

Figure 12:
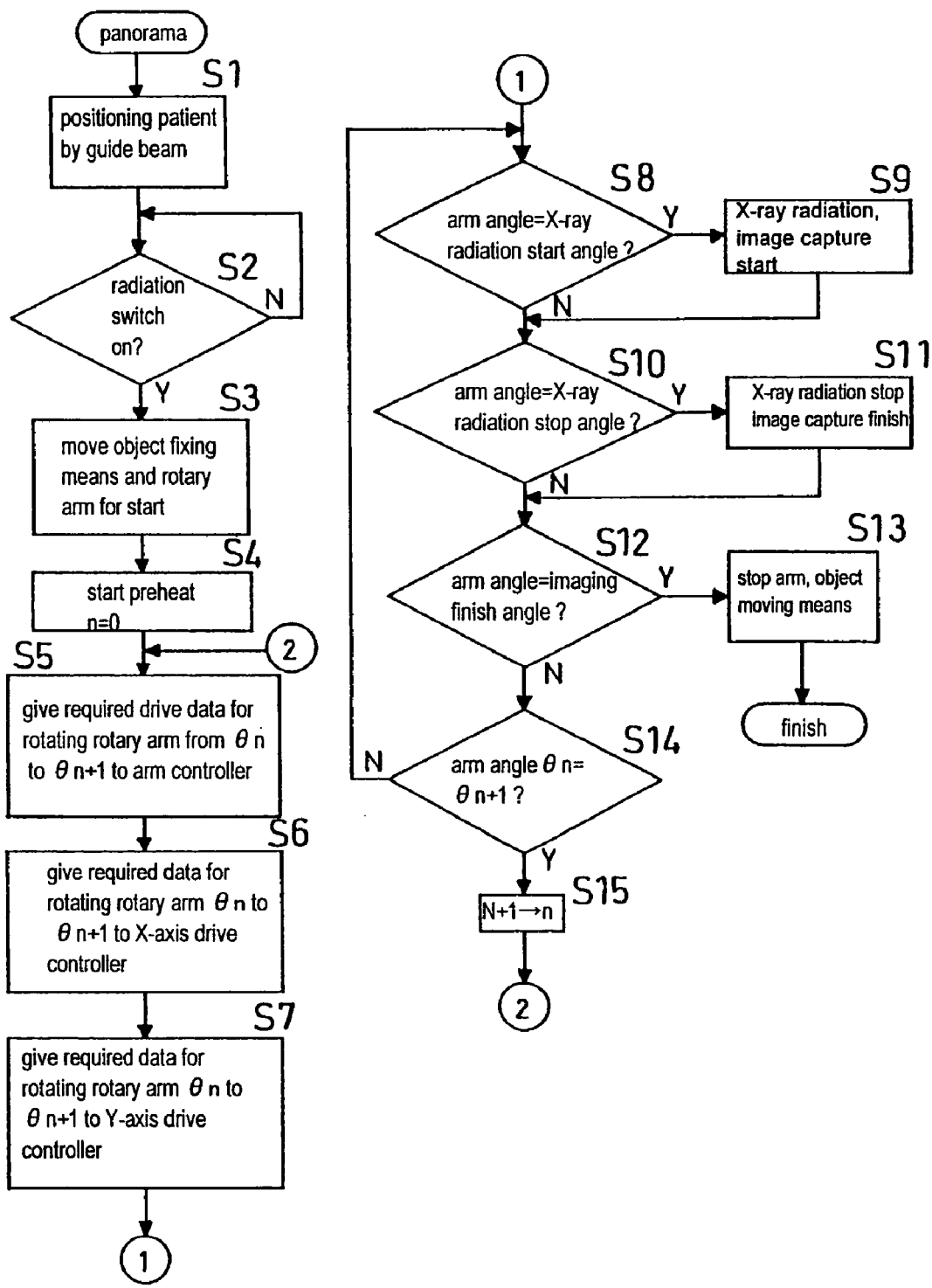
FIG. 12 is a flow chart showing the procedure of a curved plane X-ray tomography according to the X-ray CT apparatus of the present invention.

FIG. 12 is a flow chart exemplifying the procedure of a curved plane X-ray tomography according to the X-ray CT apparatus of the present invention. The procedure of the curved plane X-ray tomography by means of the X-ray CT apparatus of the present invention, which is partially explained above, is explained in order using this flow chart.

Figure 11:
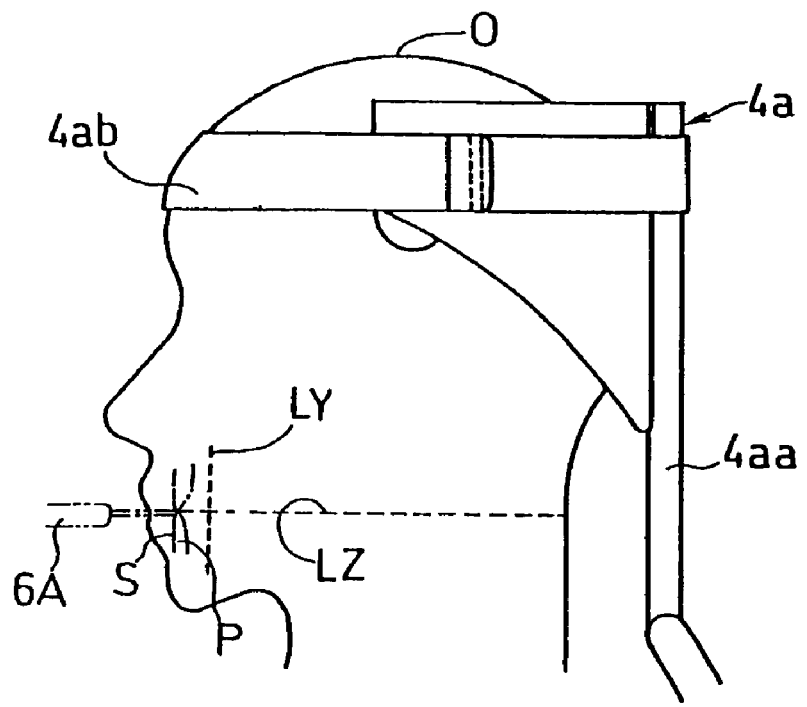
FIG. 11a is a side view when an object is fixed to an object holding means and FIG. 11b is a perspective view showing how a calibration means is used.
Figure 11:
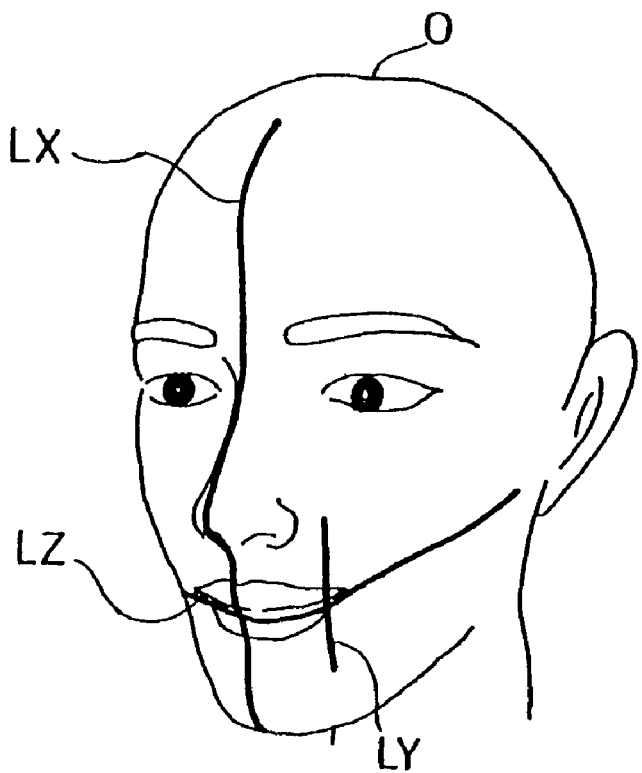

As explained in FIG. 10 and FIG. 11, at first, a patient (object) is positioned using the guide beams LX, LY, LZ as a standard, namely calibration is started (S1).

When the radiation switch 10f is pushed on (S2), the object holding means 4 is moved to an imaging start position and the rotary arm 3 is moved to an imaging start angle (S3), and preheat of the X-ray generator 1 is started and the sequence counter n is set to be "0" (S4).

Arm rotary drive data required for rotating the rotary arm 3 with a rotary angle from θn to θn+1 is given to the arm rotation controller 31f (S5).

While the rotary arm 3 is turned so as to have the rotary angle from θn to θn+1, the Y-axis drive data required for moving the Y-axis is given to the Y-axis drive controller 52f (S7).

Here, when the rotary angle of the rotary arm 3 is an X-ray radiation start angle (S8), X-ray radiation is started and capturer of the X-ray transmitted image is started (S9), if not, next procedure is started.

Here, when the rotary angle of the rotary arm 3 is an X-ray radiation stop angle (S10), X-ray radiation is stopped and capturer of the X-ray transmitted image is finished (S11), if not, next procedure is started.

Here, when the rotary angle of the rotary arm 3 is an X-ray radiation finish angle (S12), operation of the rotary arm 3 and the object moving means 5 are stopped (S13), and the curved plane X-ray tomography is finished, if not, next procedure is started.

Whether the rotary angle θn of the rotary arm 3 becomes θn+1 is checked, if not, the procedure is returned to the sequence 8 (S14), and when the rotary angle θn is θn+1, the sequence counter n+1 is set to n (S15) and the procedure is returned to sequence 5 (S5).

Thus, the curved plane X-ray tomography is executed.

Figure 13:
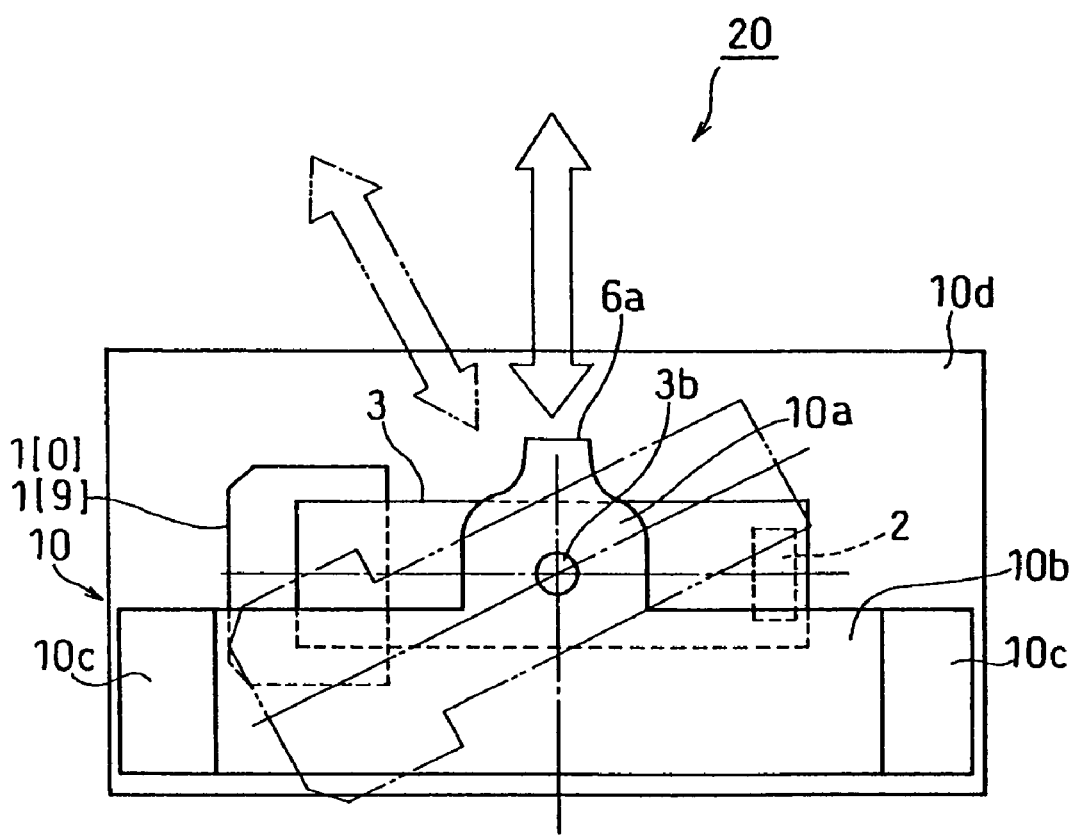
FIG. 13 is an explanatory view of an imaging start angle of a rotary arm and an imaging finish angle of a rotary arm.

FIG. 13 is an explanatory view of an imaging start angle and an imaging finish angle of a rotary arm according to the X-ray CT apparatus of the present invention.

The imaging start angle [0] and the imaging finish angle [9] of the rotary arm are designed to be an angle such that a patient easily enters or leaves under the rotary arm 3 of the apparatus in this figure. In this case, the imaging start angle [0] and the imaging finish angle [9] of the rotary arm 3 are almost the same and are perpendicular to the support body 6a projecting from the arm 10a of the main frame 10.

The rotary arm 3 starts imaging at the imaging start angle [0] and finishes imaging at the imaging finish angle [9]. Therefore, when a patient being an object O enters into and leaves from the X-ray CT apparatus 20 like the outlined arrow seen from the top of the figure, the rotary arm 3 and so on do not make an obstacle.

Depending on the setting position of the apparatus 20, it may be convenient to enter into and leave from the apparatus from the direction with two-dotted line in the figure, in such a case, the imaging start angle and imaging finish angle are the same and the rotary arm 3 is positioned perpendicular to the entering and leaving direction of the object.

In this embodiment, the imaging start angle [0] and the imaging finish position [9] are the same, however, they may be different depending on the imaging condition.

Figure 14:
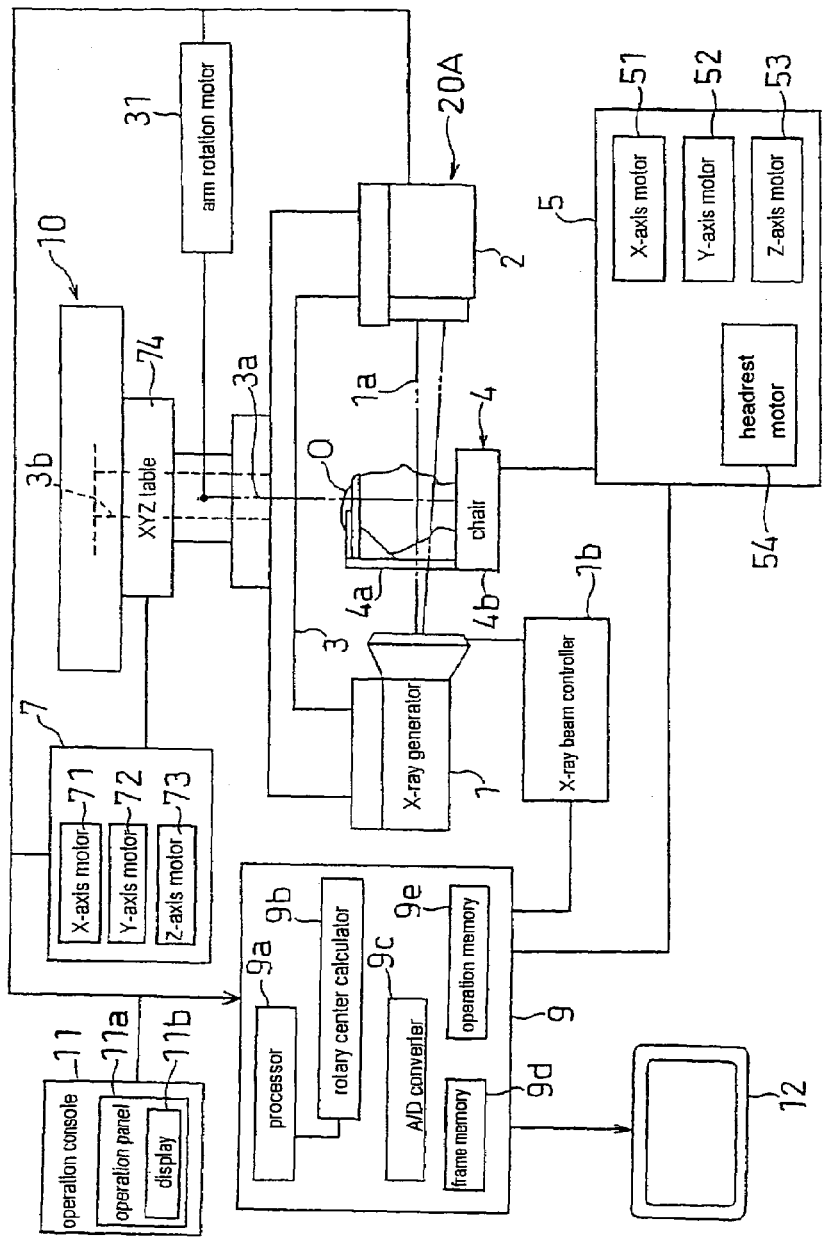
FIG. 14 shows an entire construction of other embodiment of the X-ray CT apparatus of the present invention.

FIG. 14 is shows an entire construction of other embodiment of the X-ray CT apparatus of the present invention.

The X-ray CT apparatus 20A is different from the X-ray CT apparatus 20 in FIG. 1 in that a rotary center moving means 7 is provided which is comprised of an XYZ table 74 for supporting the rotary arm 3, and an X-axis motor 71, a Y-axis motor 72 and a Z-axis motor 73 for moving the XYZ table 74 in X, Y, Z direction, respectively.

The X-axis motor 71, the Y-axis motor 72, and the Z-axis motor 73 of the rotary center moving means 7 are constructed same as the X-axis motor 51, the Y-axis motor 52, and the Z-axis motor 53 of the object moving means 5. The XYZ table 74 is constructed such that three male rail 51c, 51d, 52c, and female rails 52d, 53c, 53d of the object moving means 5 are combined respectively to slide the supported rotary arm 3 in X, Y, or Z direction accurately.

The X-ray CT apparatus 20A has thus constructed rotary center moving means 7 to move the X-ray rotary center 3a of the rotary arm 3 during X-ray circulating radiation, so that the curved plane X-ray tomography by moving the rotary center as explained in FIG. 2a can be executed.

According to the X-ray CT apparatus 20A, the first X-ray tomography and the local X-ray CT can be linked by providing the rotary center position calculation means 9b as explained in FIG. 1, FIG. 3, and FIG. 4, thereby achieving organic integration of the first X-ray tomography and the X-ray CT.

Figure 15:
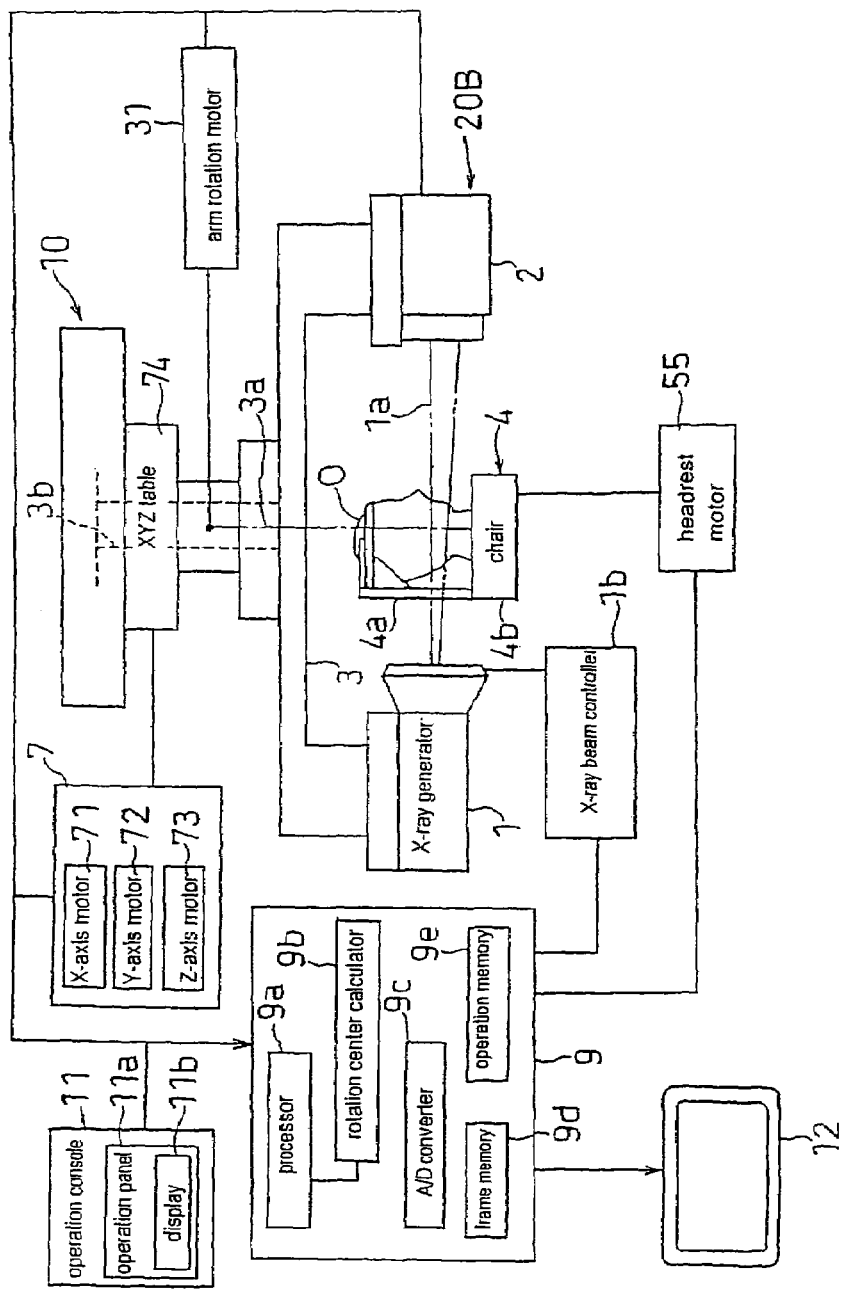
FIG. 15 shows an entire construction of other embodiment of the X-ray CT apparatus of the present invention.

FIG. 15 shows an entire construction of other embodiment of the X-ray CT apparatus of the present invention.

The X-ray CT apparatus 20B does not have the object moving means 5 comparing to the X-ray CT apparatus 20A in FIG. 14 and only a headrest motor 55 for moving the headrest 4a up and down relative to the chair 4b is provided for the object holding means 4.

The headrest motor 55 has the same construction as the headrest motor 54 included in the object moving means 5 in FIG. 14 and has the same function.

According to the X-ray CT apparatus 20B, the X-ray rotary center 3a of the rotary arm 3 can be moved by the rotary center moving means 7 while X-ray is rotationally radiated, thereby executing the curved plane X-ray tomography by moving the rotary center as explained in FIG. 2a.

As a substitute for the object moving means 5 explained in FIG. 1, the X-ray rotary center 3a may be moved, thereby relatively moving the object O and the X-ray rotary center 3a. Further, a calibration for conforming the imaging reference point of the object O and the reference point of radiography may be done, and the X-ray rotary center 3a of the rotary arm 3 may be fixed on the imaging interested area in the object O in case of CT.

Further according to the X-ray CT apparatus 20B, the first X-ray tomography and the local X-ray CT can be linked by providing the rotary center position calculation means 9b as explained in FIG. 1, FIG. 3, and FIG. 4, thereby achieving organic integration of the first X-ray tomography and the X-ray CT.

Figure 16:
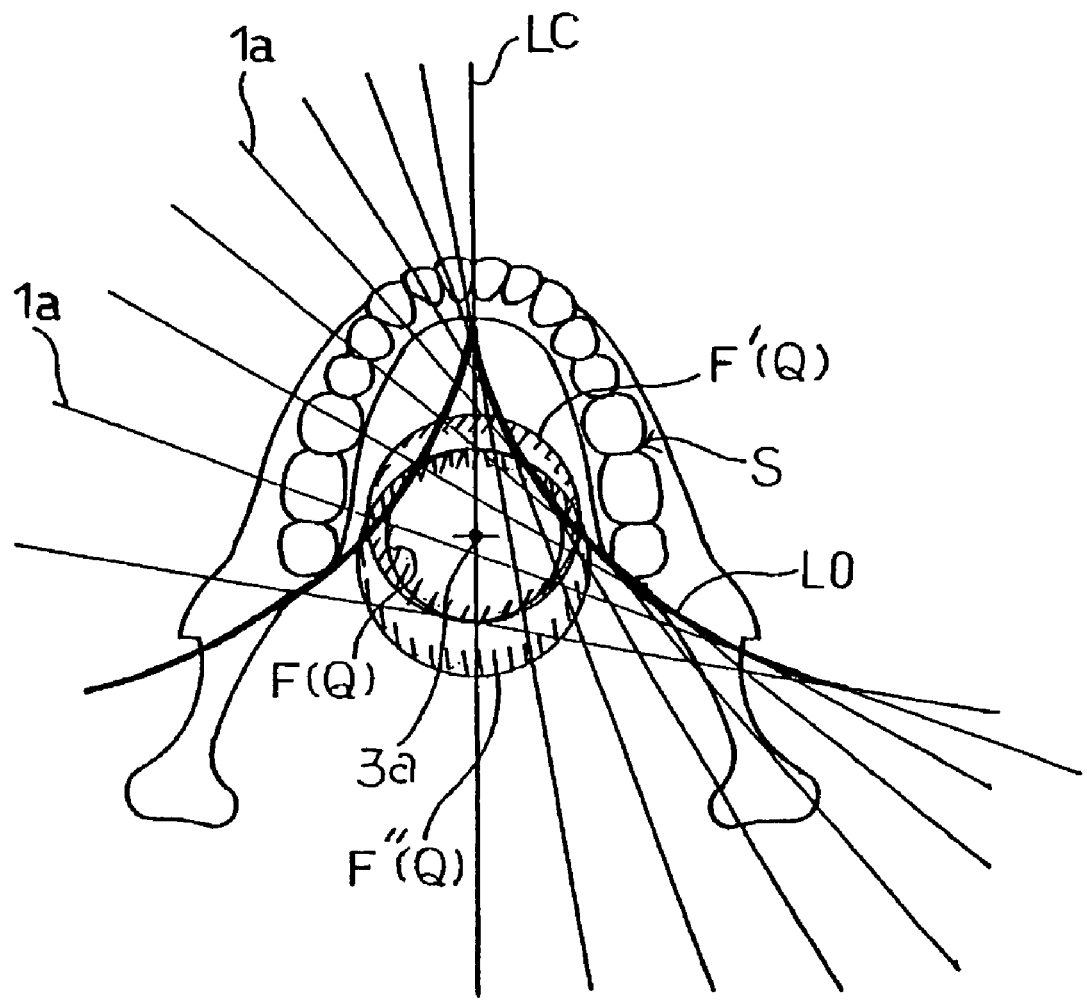
FIG. 16 is an explanatory view showing the principle of a curved plane X-ray tomography when a center of an orbit of the X-ray circulating radiation is fixed according to the X-ray CT apparatus of the present invention.

FIG. 16 is a conceptual view of a curved plane X-ray tomography when the center of the orbit of the X-ray circulating radiation is fixed according to the X-ray CT apparatus of the present invention.

In this figure, imaginary radiation regions F, F', F" and the fixed X-ray rotary center 3a are added to the same figure as FIG. 2a.

When the X-ray rotary center 3a is moved for a curved plane X-ray tomography (or the X-ray rotary center 3a and the dental arch S are relatively moved), an envelope line L0 is formed by the conical X-ray beam 1a. This is explained in FIG. 2a. The dental arch S being a radiation object is line symmetry, so that the envelope line L0 is also line symmetry. The center line LC of the line symmetry conforms to a median line of the human body, and when a circle F is drawn such that the center is on the center line LC and the circle contacts with the envelope line L0, it can be understood that all the conical X-ray beam 1a passes through the circle F.

When the conical X-ray beam 1a is radiated in a circulating manner so as to always radiate the circle F with the X-ray rotary center 3a conformed and fixed to the center of the circle F, necessary component for forming a conventional panoramic X-ray image is always included in the radiated conical X-ray beam 1a. Therefore, if the component required for forming a conventional panoramic X-ray image is extracted for image processing, the curved plane X-ray sectional image which is the same as the conventional panoramic X-ray image can be obtained. Such a method for obtaining the curved plane X-ray sectional image is called as the curved plane X-ray tomography with the X-ray rotary center fixed and is detailed in JP-A-2000-139902.

The conical X-ray beam 1a enters in substantially orthogonal direction relative to each tooth of the dental arch. The panoramic radiography in which X-ray is entered in a direction substantially orthogonal to the tooth is referred to an ortho panoramic radiography, so that the component required for forming a conventional panoramic X-ray image is called as "ortho conical X-ray beam" hereinafter.

The circle F is referred to an imaginary radiation area F and in this case, the imaginary radiation area conforms to the imaging interested area Q.

The center of the imaginary radiation area F is fluctuated along the center line LC depending on the kinds of a desired curved plane X-ray sectional image obtained by the curved plane X-ray tomography, and the area size is also fluctuated. The imaginary radiation area F corresponds to an orthodox curved plane X-ray sectional image, the imaginary radiation area F' corresponds to a standard curved plane X-ray sectional image, and the imaginary radiation area F" corresponds to a curved plane X-ray sectional image on a dental jaw.

Figure 17:
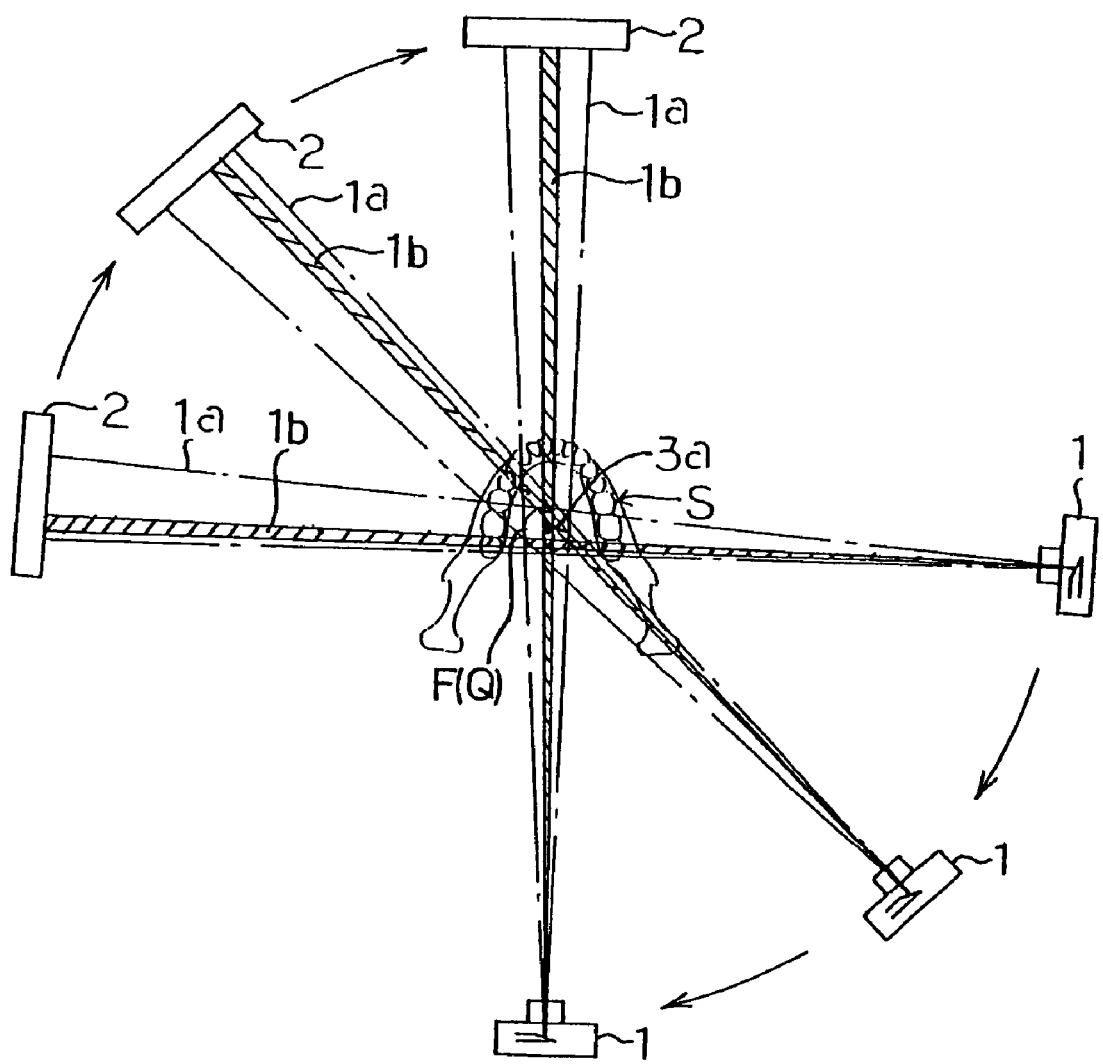
FIG. 17 is a conceptual view of a curved plane X-ray tomography when a center of an orbit of X-ray circulating radiation is fixed according to the X-ray CT apparatus of the present invention.

FIG. 17 is a conceptual view of a curved plane X-ray tomography when the center of the orbit of the X-ray circulating radiation is fixed using this concept. In the figure, the ortho conical X-ray beam is indicated as the reference numeral 1b.

In this case, the conical X-ray beam 1a is radiated in a circulating manner on the two-dimensional X-ray image sensor 2 passing through the dental arch S being an object from the X-ray generator 1 assuming the imaginary radiation area F being the imaging interested area Q and the X-ray transmitted data only by the ortho conical X-ray beam 1b are patched while arranging its pace of expansion.

Figure 18:
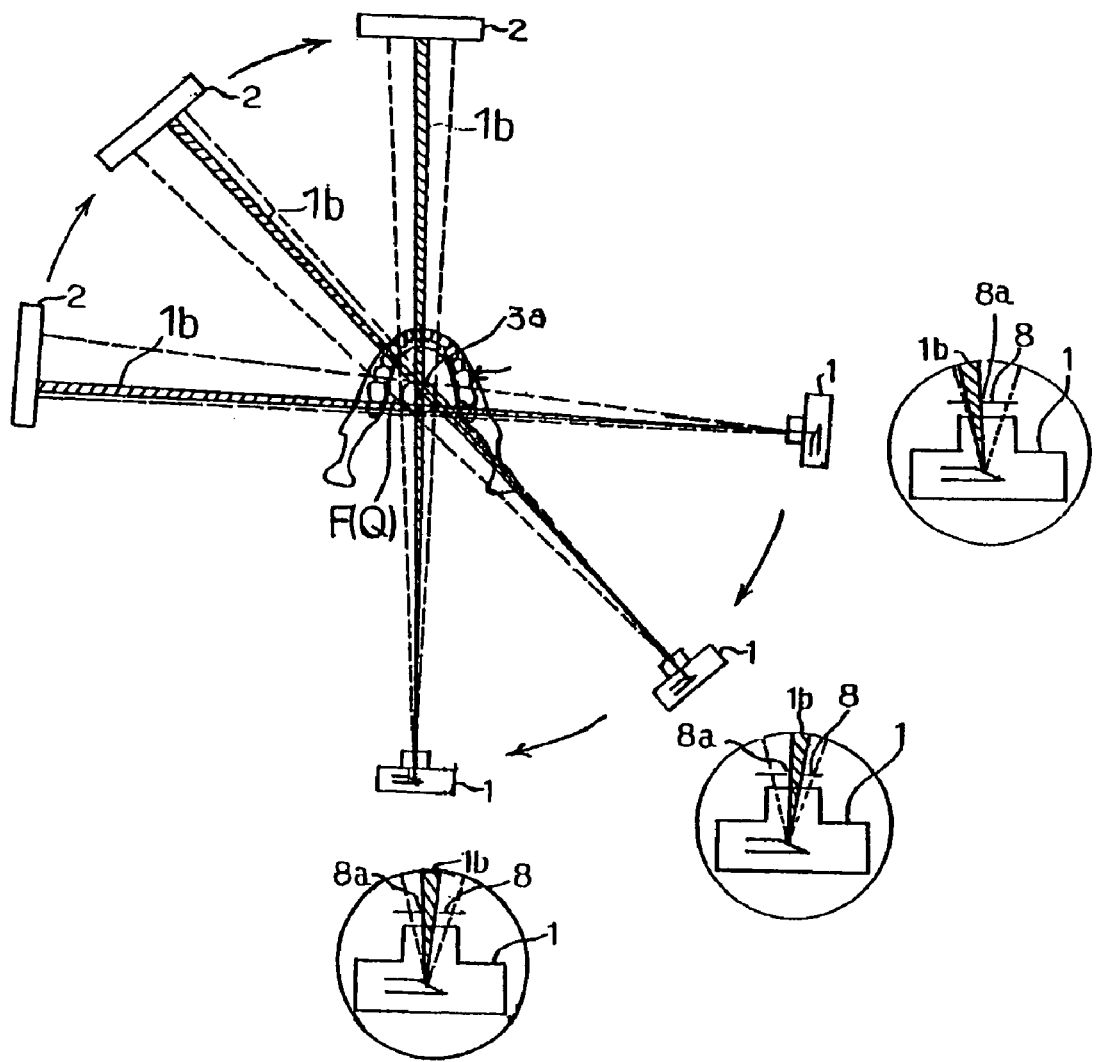
FIG. 18 is a conceptual view of a curved plane X-ray tomography when a center of an orbit of X-ray circulating radiation is fixed according to the X-ray CT apparatus of the present invention.

In FIG. 18, in the curved plane X-ray tomography of FIG. 17, further the X-ray rotary center 3a is fixed while the imaginary radiation area F and the imaging interested area Q are conformed, and a slit plate 8 with a slit 8a is provided in front of the X-ray generator 1 in such a manner that only the ortho conical X-ray beam 1b required for producing the curved plane X-ray sectional image is radiated, not the conical X-ray beam 1a covering the entire imaging interested area Q.

The slit plate 8 is movable in a rotary direction of X-ray relative to the X-ray generator 1 and is controlled to radiate only the ortho conical X-ray beam 1b depending on the rotary angle by an X-ray beam controller 1b.

Accordingly, the curved plane X-ray sectional image can be obtained like FIG. 15 and further, the X-ray exposure to the object is remarkably reduced because the conical X-ray beam 1a is changed to the ortho conical X-ray beam 1b.

Also on thus obtained curved plane X-ray sectional image, the imaging interested area Q is selected for a local X-ray CT, the apparatus 20, 20A, 20B can achieve link of the first X-ray tomography and the X-ray CT by providing the rotary center position calculation means 9b, thereby realizing an organic unification of the first X-ray tomography and the X-ray CT.

The first X-ray tomography with the center of the orbit of the X-ray circulating radiation is fixed is possible in any one of the X-ray CT apparatus 20, 20A, 20B, and the X-ray CT apparatus 20 is most preferable because the center of the orbit of the X-ray circulating radiation is fixed.

In the above embodiments, the rotary arm is used for turning the X-ray generator and the two-dimensional X-ray image sensor which are suspended and opposed, however, the X-ray generator and the two-dimensional image sensor may be provided in opposing position of a torus body like a conventional type using a gantry. Or irrespective of the supporting method of the X-ray generator and the two-dimensional X-ray image sensor, any method may be adopted if the X-ray generator and the two-dimensional image sensor are opposed and turned around the object.

The object moving means 5 of FIG. 1 and the rotary center moving means 7 of FIG. 14 and FIG. 15 are provided for moving the imaginary interested area Q relative to the object O by changing the positional relation of the object O and the X-ray rotary center 3a by relatively moving the object O fixed with the object holding means 4 and the X-ray rotary center 3a, namely by moving the object O, the X-ray rotary center 3a or both of them. Both of them are referred to an imaging area moving means.

As for the moving direction of the object moving means, the object is moved a horizontally corresponding to the vertical type X-ray CT apparatus in the above embodiments, however, when the apparatus is a traverse type, the object moving means moves an object on a vertical flat plane. In principle, the object moving means moves the object in the rotary plane direction formed by the X-ray circulating radiation.

The X-ray CT apparatus of the present invention is applicable to not only a dental field as explained hereinbefore, but also other diagnosis field like otolaryngology, the case for the object like hands, arms, and excised organ, animals such as dogs and cats. Further, the apparatus is also applicable to a general nondestructive test.

More specifically, the above-mentioned embodiments are explained such that the present invention is applied to both of a panoramic radiography of a dental arch and an X-ray CT of a tooth included in the dental arch in the field of dentistry. The similar method can be executed for the curved plane X-ray tomography and X-ray CT of auditory ossicle in the field of otolaryngology and the same effects are achieved.

Next explained is a method for linking the X-ray sectional image obtained by the first X-ray tomography and the X-ray sectional image obtained by the second X-ray tomography, namely associating the images each other, and for invoking and displaying.

Figure 20:
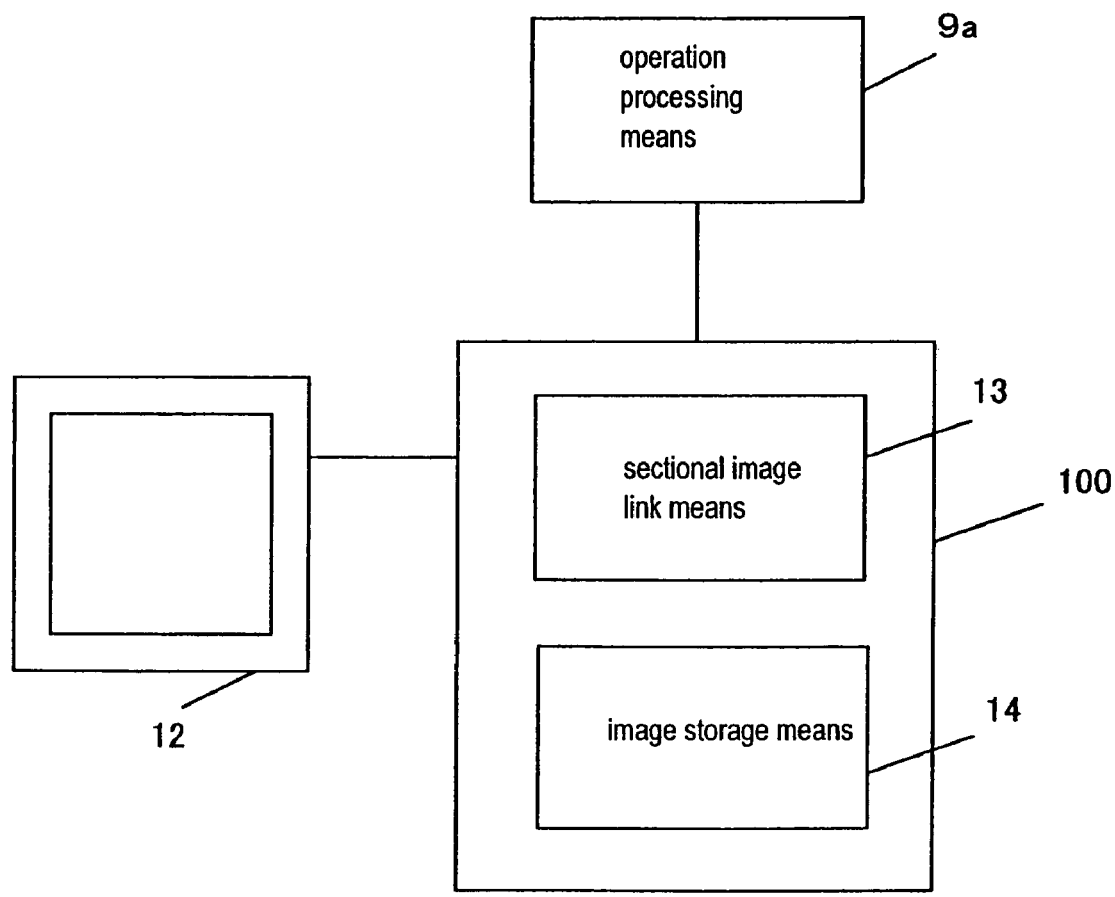
FIG. 20 is a block diagram showing a basic construction of other link means provided for the X-ray CT apparatus of the present invention.

The corresponding image calling means 100 shown in FIG. 20 is provided with a sectional image link means 13 and an image recording means 14.

The sectional image link means 13 subdivides the X-ray CT image obtained by the first X-ray tomography into an assembly of the X-ray sectional image comprised of plural X-ray sectional images hewn out in advance at a fixed interval at least in one direction among the three-dimensional directions (X, Y, Z axis direction) and links each X-ray sectional image in the assembly of the X-ray sectional image as the second X-ray sectional image corresponding to the imaging region of the first X-ray sectional image obtained by the first X-ray tomography.

Figure 21:
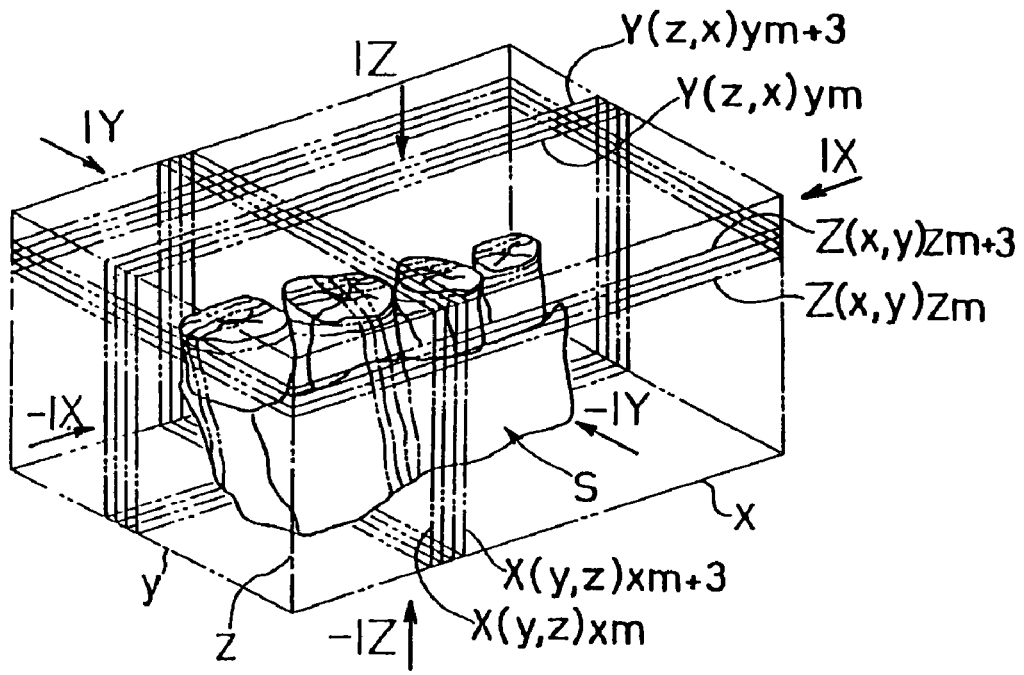
FIG. 21a explains the principle when a sectional image is hewn out of a three-dimensional X-ray CT data and FIG. 21b is an explanatory view of a display method of a sectional image.
Figure 21:
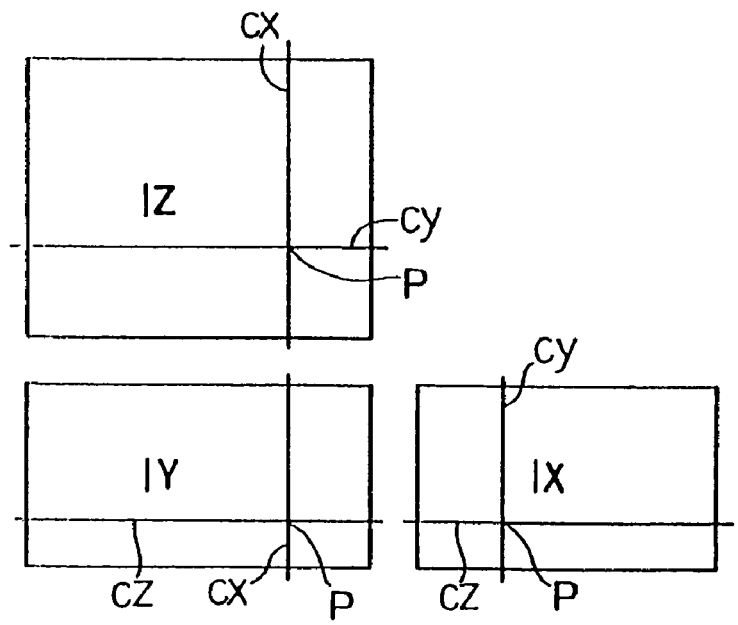

This is explained in more detail referring to FIG. 21.

FIG. 21a conceptually explains how a sectional image is hewn out in the sectional image display method of the present invention and FIG. 21b is a conceptual view of a display method in the sectional image display method of the present invention. The members which have been already explained have the same numerals and their explanations are omitted.

A three-dimensional CT data is obtained for each point comprising three-dimensional area S (explained later) shown in FIG. 21a and when an xyz coordinate system is set as shown in the figure for the three-dimensional area S, the voxel value V(s, y, z) on an optional point (x, y, z) is determined on the xyz coordinate system.

The plane vertical to the x-axis is referred to an X sectional plane, x-coordinate (x=xm) is determined and the voxel value V(xm, y, z) on the X sectional plane having the x-coordinate is arranged on a two-dimensional flat plane for hewing out the X sectional image relative to the X sectional plane. The X sectional image on the plane perpendicular to the x-axis obtained by the voxel value is described as X(y,z)xm.

According to this method, X(y,z)x0, X(y,z)x1, . . . , X(y,z)xm, X(y,z)xm+1, X(y,z)xm+2, X(y,z)xm+3, . . . , X(y,z)xn, are obtained.

Similarly, a Y sectional image on a Y sectional plane perpendicular to a y-axis is obtained like Y(z,x)y0, Y(z,x)y1, . . . , Y(z,x)ym, Y(z,x)ym+1, Y(z,x)ym+2, Y(z,x)ym+3, . . . , Y(z,x)yn, and a Z sectional image on a Z sectional plane perpendicular to a z-axis is obtained like Z(x,y)z0, Z(x,y)z1, . . . Z(x,y)zm, Z(x,y)zm+1, Z(x,y)zm+2, Z(x,y)zm+3, . . . , Z(x,y)zn.

The sectional image link means 13 of the corresponding image calling means 100 links plural sectional images, namely each X-ray sectional image in the assembly of the X-ray sectional image as the second sectional image corresponding to each imaging region of the first X-ray sectional image obtained by the first X-ray tomography. The image recording means 14 stores the first X-ray sectional image and the second X-ray sectional image corresponding each other together with the positional information like coordinate defined by X, Y and Z directions of each imaging region.

An optional sectional image including an optional point P in the three-dimensional area S among thus obtained X, Y, or Z sectional images is taken out and FIG. 21b shows them together with an X-cursor cx, a Y-cursor cy, and Z-cursor cz.

Figure 22:
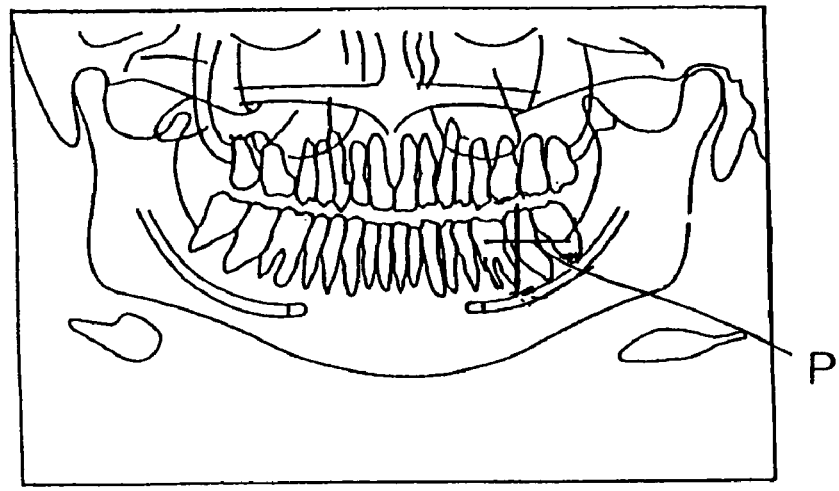
FIG. 22a exemplifies an X-ray transmitted image obtained by the first tomography and FIG. 22b is a conceptual view of a curved plane X-ray tomography when a center of an orbit of X-ray circulating radiation is fixed according to the X-ray CT apparatus of the present invention.
Figure 22:
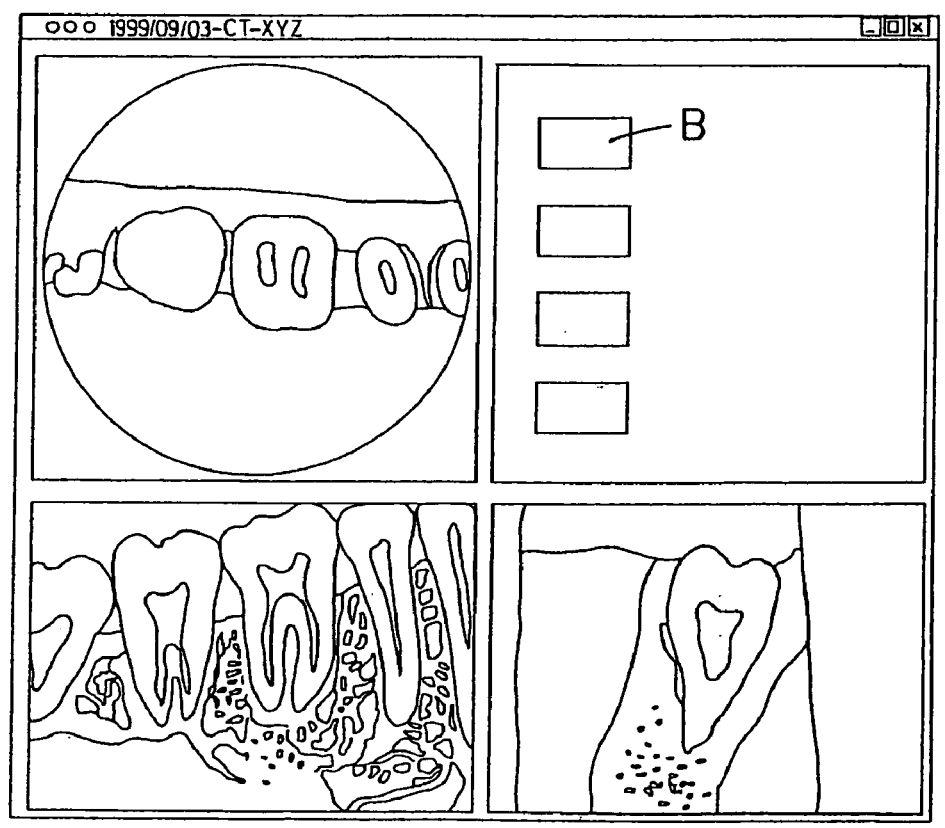

The procedure shown in FIG. 22 is required for executing the above-mentioned process in the second X-ray tomography.

When a cross pointer P shown in a dental panoramic image or the curved plane X-ray sectional image for otolaryngology obtained by the first X-ray tomography is moved as shown in FIG. 22a, the X-ray sectional image hewn in advance corresponding to the position according to the above-mentioned procedure, namely the corresponding second X-ray sectional image, which is obtained by the second X-ray tomography and is linked with the first X-ray sectional image by the sectional image link means 13, is invoked by the corresponding image calling means 100 to be shown like FIG. 22b.

The second sectional image shown on the display 12 is returned into the original panoramic X-ray image or curved plane sectional image for otolaryngology when the panoramic image display button B is operated.

According to the corresponding image calling means 100, the dental panoramic image or the curved plane X-ray sectional image for otolaryngology obtained by the first X-ray tomography and the X-ray CT image obtained by the second X-ray tomography on the corresponding imaging area are displayed linking each other, and the first X-ray sectional image obtained by the first X-ray tomography and the linked second X-ray sectional image obtained by the second X-ray tomography can be displayed.

Figure 25:
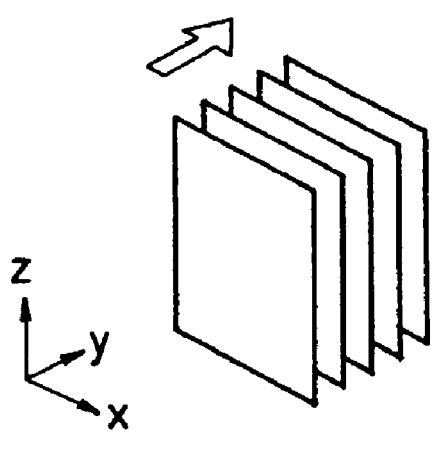
FIG. 25a shows an embodiment in which the image is hewn out at a fixed interval at least in one direction among an X-axis direction, a Y-axis direction and a Z-axis direction
FIG. 25b shows an embodiment in which an axis CTR is determined in an imaging interested area and the image is hewn out by image processing so as to be rotated around the axis CTR.
Figure 25:
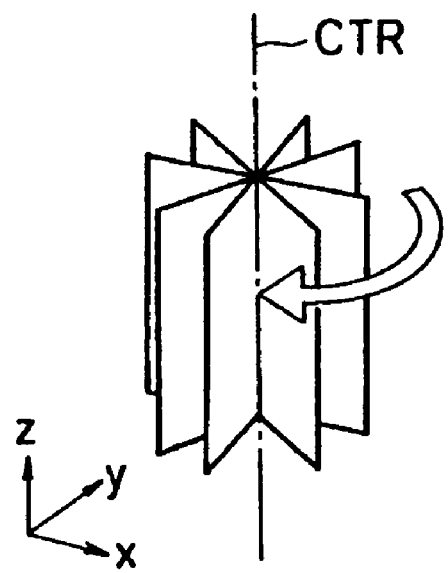

In the abovementioned embodiment, the hewing direction of the image is at least one direction among the X, Y, and Z axis directions at a fixed interval as shown in FIG. 25a, however, the image may be hewn out by image processing by rotating around an axis CTR which is set in the imaging interested area.

Figure 19:
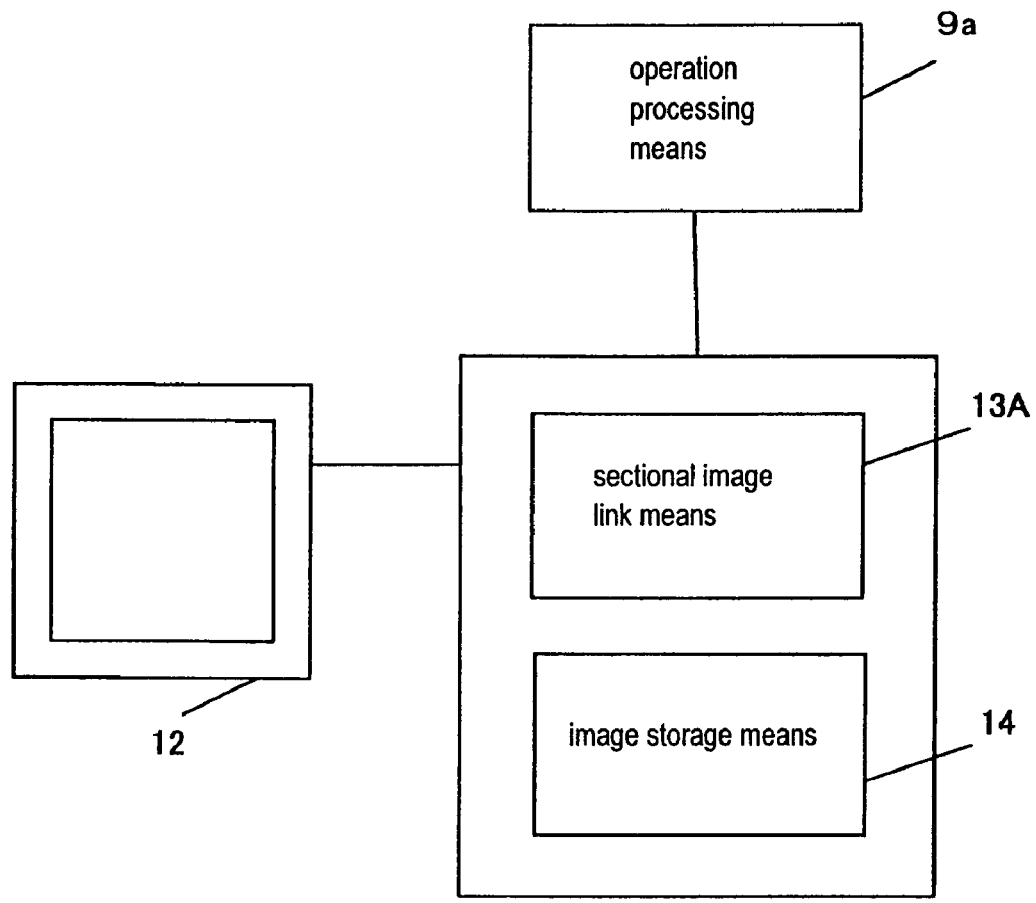
FIG. 19 is a block diagram showing a basic construction of a link means provided for the X-ray CT apparatus of the present invention.

In the link means shown in FIG. 19 link display is manually done by an operator. A sectional image link setting means 13A is added other than the image recording means 14.

The sectional image link setting means 13A displays an optional X-ray sectional image among the first X-ray sectional images obtained by the first X-ray tomography and an optional X-ray sectional image among the second X-ray sectional images obtained by the second X-ray tomography on the display 12 and they are linked each other by the sectional image link means. Link operation is done by the operation console (FIG. 1) by an operator.

The image recording means 14 stores the first X-ray sectional image and the second X-ray sectional image together with positional information. Thus the first X-ray sectional image and the second X-ray sectional image are optionally linked.

INDUSTRIAL APPLICABILITY

According to the X-ray CT apparatus of the present invention, the object holding means fixing the object is moved by the object moving means along the first X-ray sectional image producing orbit depending on the rotary angle of the rotary arm during the X-ray circulating radiation X-ray.

The center of the orbit of the X-ray circulating radiation is fixedly held, so that deflection of the rotary center is not caused, and the deflection does not cause accuracy deterioration of the second X-ray tomography, namely the X-ray CT.

Further, the object is moved along the first X-ray sectional image producing image orbit, so that the X-ray transmitted image obtained such radiation can be patched without arranging the pace of expansion and executing time-consuming back projection, thereby obtaining the X-ray sectional image on a curved plane or a flat plane similar to the conventional one.

Further according to the X-ray CT apparatus of the present invention, when the imaging interested area is selected on the first X-ray sectional image, the object moving means moves the object holding means, namely the object, by the center movement data obtained by the rotary center position calculation means in such a manner that the center of the orbit of the X-ray circulating radiation is fixed on a predetermined point in the selected imaging interested area.

Therefore, the time from start of the first X-ray tomography to completion of CT on the selected imaging interested area of the object is remarkably short, so that the interested area to be imaged by X-ray CT can be specified and X-ray CT can be executed for the imaging interested area following the first X-ray tomography without imposing a burden on a patient while the object is held with the object holding means, thereby achieving skilful link of the first X-ray tomography and X-ray CT, namely the second X-ray CT.

Still further according to the X-ray CT apparatus of the present invention, the first X-ray tomography is for obtaining the X-ray sectional image including the blurred image of the region other than the objective sectional plane and the second X-ray tomography is a computed tomography in which a three-dimensional X-ray absorption coefficient data is computer processed, namely an X-ray tomography for obtaining the X-ray sectional image excluding the blurred image. Therefore, the X-ray absorption distribution is digitally obtained for the X-ray sectional plane relative to the X-ray sectional image of the interested area imaged by the second X-ray tomography and the X-ray sectional image without having the blurred images can be obtained from the X-ray absorption distribution information. As a result, the X-ray sectional image excluding the blurred image can be obtained in case of the X-ray tomography on the interested area which is usually required to obtain an accurate X-ray sectional image, thereby contributing accurate diagnosis.

Still further according to the X-ray CT apparatus of the present invention, after the first X-ray tomography is finished, the local region of the object is imaged by moving the interested area of the object. Thus, the link of the first X-ray tomography and the second X-ray tomography is possible.

Still further according to the X-ray CT apparatus of the present invention, after the first X-ray tomography, the interested area of the object to be imaged is easily specified on the display means.

Still further according to the X-ray CT apparatus of the present invention, the start and termination angles of X-rau circulating radiation are set appropriate in such a manner that a patient easily enters in or leaves from the apparatus. The rotary arm is automatically set at the start angle before imaging and is automatically set at the termination angle after imaging, so that the arm does not become an obstacle when the patient enters in or leave from, thereby being convenient.

Still further according to the X-ray CT apparatus of the present invention, the curved plane X-ray tomography is specifically limited to a dental panoramic radiography and the curved plane X-ray tomography for otolaryngology. The curved plane X-ray sectional tomography is done for a dental arch in the field of dentistry and is done for auditory ossicle in the filed of otolaryngology.

Still further according to the X-ray CT apparatus of the present invention, the X-ray sectional image obtained by the first X-ray tomography and the second X-ray sectional image obtained by the X-ray CT are linked each other to be optionally invoked and displayed.

The invention claimed is:

1. An X-ray computer tomography apparatus having an X-ray radiation means comprising an X-ray generator and a two-dimensional X-ray image sensor,
    wherein an X-ray beam is radiated on an object to be examined for X-ray circulation radiation, while said X-ray generator and said two-dimensional X-ray image sensor move around said object with said object interposed therebetween, so as to keep their mutual facing positional relation, and
    wherein said X-ray tomography apparatus is configured to execute a first X-ray tomography for obtaining a panoramic image and configured to execute a second X-ray tomography for obtaining a computed tomography image of an interested area of said object;
    said X-ray computer tomography apparatus further comprising:
        an object holding means on which said object is set up, said object holding means being moved by an object moving means; and
        a processing means configured to control said object moving means to move said object holding means depending on the changing of rotary angle of said X-ray radiation means, and configured to execute said first X-ray tomography, while said X-ray radiation means rotates around said object during execution of said first X-ray tomography, with a rotaty center of said X-ray radiation means being fixed relative to said apparatus.

2. The X-ray computer tomography apparatus as set forth in claim 1, wherein said X-ray computer tomography apparatus further comprises an image processing means for producing an X-ray sectional image by executing Time Delay Integration (TDI) processing to an X-ray transmitted image detected by said two-dimensional X-ray image sensor in said first X-ray tomography, which is transmitted through said object by radiating X-rays from said X-ray generator.

3. The X-ray computer tomography apparatus as set forth in claim 1,
    wherein said first X-ray tomography is executed for obtaining an X-ray sectional image including a blurred image of regions other than a target sectional area through a curved plane tomography or a flat plane tomography in a manner such that said X-ray generator and said two-dimensiomal X-ray image sensor are moved around an object to be examined, with said object interposed therebetween, so as to hold their mutual facing positional relation, and
    wherein said second X-ray tomography is executed for obtaining an X-ray sectional image excluding a blurred image through computed tomography which computes and processes three-dimensional X-ray absorption coefficient data.

4. The X-ray computer tomography apparatus as set forth in claim 1, wherein movement of said X-ray generator and said two-dimensional X-ray image sensor is a rotary movement or a parallel movement.

5. The X-ray computer tomography apparatus as set forth in claim 1, wherein said second X-ray tomography is executed for obtaining an X-ray computed tomography image around a local region of said object in a manner such that the interested area of said object conforms to the rotary center of X-ray circulating radiation by moving said object holding means or said X-ray radiation means after said first X-ray tomography is finished.

6. The X-ray computer tomography apparatus as set forth in claim 1, comprising:
    a display means on which a first X-ray sectional image of said object taken by said first X-ray tomography is displayed, and an interested area selection means for selecting the interested area to be taken by said second X-ray tomography on said first X-ray sectional image displayed on said display means; and
    a calculation means of rotary center position for calculating movement data for relatively moving said object holding means or said X-ray radiation means in a manner such that an X-ray rotary center conforms to said interested area selected by said interested area selection means;
    wherein said object holding means or said X-ray radiation means is moved depending on said movement data, and thereafter said X-ray radiation means is circulated with the center of the orbit of the X-ray circulating radiation fixedly conformed to said interested area during X-ray circulating radiation, thereby executing said second X-ray tomography.

7. The X-ray computer tomography apparatus as set forth in claim 6, wherein a position guide index or an area guide index for selecting the interested area is shown on the first X-ray sectional image displayed on said display means and the interested area is selected by selecting operation of the position guide index or movement operation of said area guide index.

8. The X-ray computer tomography apparatus as set forth in claim 6, wherein said interested area selection means is constructed so as to be able to display a diagram of an imaging region corresponding to the first X-ray sectional image and an interested area index movable on the diagram displayed on said display means, and wherein said interested area to be selected for X-ray CT is constructed so as to be able to be specified by moving operation or selecting operation of said interested area index on the diagram shown.

9. The X-ray computer tomography apparatus as set forth in claim 1, wherein said object holding means has a chair for holding a patient in sitting position and a head fixing means at the upper part of the chair, and wherein said object holding means further has a pulse motor for moving said object in an axial direction of an X-ray rotary axis or in a vertical direction to the X-ray rotary axis.

10. The X-ray computer tomography apparatus as set forth in claim 9, wherein said X-ray radiation means has a rotary arm rotatable around the rotary center, said rotary arm holding said X-ray generator and said two-dimensional X-ray imaging sensor so as to keep their mutual facing positional relation, and wherein said first X-ray tomography is executed for obtaining a curved plane sectional image in a manner such that said rotary arm turns around the object with the center of the orbit of the X-ray circulating radiation fixed during said first X-ray tomography, while said chair is moved along a predetermined imaging orbit in synchronism with the turning of said rotary arm.

11. The X-ray computer tomography apparatus as set forth in claim 1, wherein said first X-ray tomography is executed for obtaining a flat plane sectional image by mutually moving said X-ray generator and said two-dimensional X-ray image sensor held by a rotary arm in a direction opposite to each other, while turning said rotary arm around said object with said interested area interposed therebetween.

12. The X-ray computer tomography apparatus as set forth in claim 1, wherein said second X-ray tomography is executed for obtaining an X-ray computer tomography image of a local region of said object by radiating a conical X-ray beam from said X-ray generator.

13. The X-ray computer tomography apparatus as set forth in claim 1, wherein said two-dimensional X-ray imaging sensor is comprised of any one of CdTe, MOS, CCD, XII, XICCD, or a photo diode array.

14. The X-ray computer tomography apparatus as set forth in claim 1, wherein start and termination angles of the X-ray circulating radiation are set in such an appropriate position or an angle for a patient to easily come in and out of said object holding means corresponding to said first and said second X-ray tomography, respectively.

15. The X-ray computer tomography apparatus as set forth in claim 1, wherein an X-ray beam switching means is provided for switching a shape of an X-ray beam radiated from said X-ray generator in the first X-ray tomography and a shape of an X-ray beam radiated from said X-ray generator in the second X-ray tomography.

16. The X-ray computer tomography apparatus as set forth in claim 1, wherein said curved plane X-ray tomography is executed for obtaining a dental panoramic image or a curved sectional X-ray image for use in otolaryngology.

17. The X-ray computer tomography apparatus as set forth in claim 1, said X-ray computed tomography apparatus comprising:

a sectional image link means for subdividing in advance a second X-ray sectional image obtained by said second X-ray tomography into an assembly of X-ray sectional images comprised of plural X-ray sectional images cut out at a fixed interval at least in one direction of three dimensional directions and for linking each X-ray sectional image in said assembly of the X-ray sectional images as the second X-ray sectional image to the first X-ray sectional image obtained by said first X-ray tomography corresponding to an imaging region;

an image recording means for storing together with each positional information said first X-ray sectional image and said second X-ray sectional image, each linked to the corresponding information; and a corresponding image calling means for invoking the linked corresponding X-ray sectional image when at least one of said first X-ray sectional image and said second X-ray sectional image stored in said image recording means is read out and is shown on said display means.

18. The X-ray computer tomography apparatus as set forth in claim 17, wherein said second X-ray sectional image subdivided into the assembly of plural X-ray sectional images is capable of being sequentially reproduced and displayed at least in one direction of three dimensional directions by moving operation of a cursor on said display means, and wherein the linked corresponding X-ray sectional image is invoked from said corresponding image calling means when at least one of said first X-ray sectional image and said second X-ray sectional image stored in said image recording means is read out and shown on said display means.

19. The X-ray computer tomography apparatus as set forth in claim 17, wherein said first X-ray sectional image is a dental panoramic X-ray image.

20. The X-ray computer tomography apparatus as set forth in claim 17, wherein the X-ray sectional image corresponding to said first X-ray sectional image and/or the second X-ray sectional image are/is read out to be displayed on a part of said display means, when at least one of the first X-ray sectional image and the second X-ray sectional image stored in said image recording means is read out and displayed on said display means.

21. The X-ray computer tomography apparatus as set forth in claim 1, wherein said object holding means is movable in an axial direction of the X-ray rotary axis as well as in a vertical direction to the X-ray rotary axis.

* * * * *